US012169350B2

(12) United States Patent
Walukas et al.

(10) Patent No.: US 12,169,350 B2
(45) Date of Patent: Dec. 17, 2024

(54) APPARATUS FOR ANALYZING A MEDIA, AND ASSOCIATED EGG IDENTIFICATION APPARATUS AND METHOD

(71) Applicant: Zoetis Services LLC, Parsippany, NJ (US)

(72) Inventors: Joel James Walukas, Cary, NC (US); Daniel Wickstrom, Cary, NC (US); Amanda Elizabeth Basciano, Apex, NC (US)

(73) Assignee: Zoetis Services LLC, Parsippany, NJ (US)

( * ) Notice: Subject to any disclaimer, the term of this patent is extended or adjusted under 35 U.S.C. 154(b) by 1089 days.

(21) Appl. No.: 16/049,926

(22) Filed: Jul. 31, 2018

(65) Prior Publication Data

US 2019/0041722 A1 Feb. 7, 2019

Related U.S. Application Data

(60) Provisional application No. 62/539,684, filed on Aug. 1, 2017.

(51) Int. Cl.
*G02F 2/00* (2006.01)
*G01J 3/10* (2006.01)
(Continued)

(52) U.S. Cl.
CPC ............... *G02F 2/004* (2013.01); *G01J 3/10* (2013.01); *G01J 3/427* (2013.01); *G01N 17/004* (2013.01);
(Continued)

(58) Field of Classification Search
CPC ... G02F 2/004; G01J 3/10; G01J 3/427; G01J 2003/104; G01J 9/00; G01N 17/004;
(Continued)

(56) References Cited

U.S. PATENT DOCUMENTS 2,823,800 A * 2/1958 Bliss ................... G01N 33/085
209/912
3,031,077 A 4/1962 Mumma et al.
(Continued)

FOREIGN PATENT DOCUMENTS

CA 3069323 A1 * 2/2019 ........... F25J 3/04193
CN 104330189 A 2/2015
(Continued)

OTHER PUBLICATIONS

PCT International Search Report and Written Opinion, International Application No. PCT/US2018/043996, International Filing Date Jul. 27, 2018, Date of mailing Nov. 12, 2018.
(Continued)

*Primary Examiner* — Mohamed K Amara
(74) *Attorney, Agent, or Firm* — Scott C. Mayhew

(57) ABSTRACT

An apparatus for interrogating a media to be analyzed, such as an avian egg, is provided. Such an apparatus includes an emitter assembly configured to emit light toward a media. The emitter assembly has a first emitter source configured to emit a first light signal and a second emitter source configured to emit a second light signal. The first and second light signals are transmitted through the media in phase quadrature. A detector assembly is configured to detect the first and second light signals transmitted through the media. The detector assembly is further configured to resolve a relative or absolute amplitude of each of the first and second light signals. A processor is configured to process the detected signal to identify a property of the media using at least one of the relative and absolute amplitudes of the first and second light signals. An associated method is also provided.

14 Claims, 17 Drawing Sheets

(51) Int. Cl.
| | |
|---|---|
| *G01J 3/427* | (2006.01) |
| *G01N 17/00* | (2006.01) |
| *G01N 21/25* | (2006.01) |
| *G01N 21/31* | (2006.01) |
| *G01N 33/08* | (2006.01) |
| *G02B 27/14* | (2006.01) |

(52) U.S. Cl.
CPC ........... *G01N 21/256* (2013.01); *G01N 21/31* (2013.01); *G01N 21/3151* (2013.01); *G01N 33/085* (2013.01); *G02B 27/141* (2013.01); *G01J 2003/104* (2013.01); *G01N 2021/3155* (2013.01)

(58) Field of Classification Search
CPC .. G01N 21/256; G01N 21/31; G01N 21/3151; G01N 33/085; G01N 2021/3155; G01N 21/25; G01N 33/08; G01N 2201/06113; G01N 33/4833; G01N 2021/6419; G01N 21/49; G02B 27/141; G02B 26/06; A01K 43/00; G06K 9/00557; G06T 2207/30044; G06T 2207/30004; H01S 3/10053; H01S 3/0085

See application file for complete search history.

(56) References Cited

U.S. PATENT DOCUMENTS

| | | | | |
|---|---|---|---|---|
| 3,130,255 | A * | 4/1964 | Blackburn | G01N 21/314 356/53 |
| 3,930,994 | A * | 1/1976 | Conway | B07C 5/3416 209/579 |
| 4,039,259 | A | 8/1977 | Saito et al. | |
| 4,063,822 | A | 12/1977 | deJong et al. | |
| 4,182,571 | A * | 1/1980 | Furuta | G01N 33/085 356/53 |
| 4,391,373 | A * | 7/1983 | Wiggins | G01N 21/9054 209/588 |
| 4,586,026 | A | 4/1986 | Braig et al. | |
| 4,807,630 | A * | 2/1989 | Malinouskas | G01N 21/3151 600/323 |
| 4,846,183 | A * | 7/1989 | Martin | G01N 21/3151 356/41 |
| 5,321,491 | A * | 6/1994 | Summers | G01N 33/085 382/110 |
| 5,349,952 | A * | 9/1994 | McCarthy | A61B 5/417 600/479 |
| 5,745,228 | A * | 4/1998 | Hebrank | A01K 45/007 250/341.1 |
| 5,774,213 | A * | 6/1998 | Trebino | G01N 21/3151 356/41 |
| 5,800,348 | A * | 9/1998 | Kaestle | A61B 5/14551 600/323 |
| 5,995,858 | A | 11/1999 | Kinast | |
| 6,504,603 | B1 * | 1/2003 | Schouenborg | G01N 33/085 356/53 |
| 6,535,277 | B2 * | 3/2003 | Chalker, II | A01K 43/00 356/53 |
| 7,904,139 | B2 | 3/2011 | Chance | |
| 8,219,170 | B2 * | 7/2012 | Hausmann | G01J 3/10 600/323 |
| 8,624,190 | B2 * | 1/2014 | Steiner | G01N 21/552 250/339.08 |
| 9,179,651 | B2 * | 11/2015 | McKay | G01N 33/08 |
| 10,060,854 | B2 * | 8/2018 | Schortgen | G01N 33/085 |
| 10,684,591 | B1 * | 6/2020 | Burke | H01S 3/1303 |
| 2002/0075476 | A1 | 6/2002 | Chalker, II et al. | |
| 2003/0227613 | A1 | 12/2003 | Hebrank | |
| 2009/0091742 | A1 * | 4/2009 | Hebrank | G01N 33/085 356/53 |
| 2010/0078560 | A1 | 4/2010 | Basham | |
| 2012/0002204 | A1 | 1/2012 | Varghese et al. | |
| 2013/0004421 | A1 * | 1/2013 | Capala | A61P 19/04 530/300 |
| 2013/0286390 | A1 * | 10/2013 | Bolles | G01J 3/12 356/326 |
| 2014/0070077 | A1 * | 3/2014 | Tsuchimoto | G01J 1/44 250/214 A |
| 2014/0269790 | A1 * | 9/2014 | Sebastian | G01J 9/02 372/20 |
| 2015/0042985 | A1 | 2/2015 | Chiarello et al. | |
| 2015/0138533 | A1 * | 5/2015 | Bolles | G01J 3/0237 356/326 |
| 2016/0239953 | A1 * | 8/2016 | Ngadi | G06K 9/629 |
| 2017/0261426 | A1 * | 9/2017 | Hirata | G01N 21/35 |
| 2019/0041722 | A1 * | 2/2019 | Walukas | G01N 17/004 |
| 2019/0226985 | A1 * | 7/2019 | Roberts | G01N 21/274 |
| 2020/0400640 | A1 * | 12/2020 | Preusse | G06V 10/145 |
| 2021/0173189 | A1 * | 6/2021 | Sun | G02B 21/02 |
| 2023/0296438 | A1 * | 9/2023 | Jasperse | G01J 3/10 356/326 |

FOREIGN PATENT DOCUMENTS

| | | | |
|---|---|---|---|
| CN | 105530809 A | | 4/2016 |
| CN | 105849552 A | | 8/2016 |
| CN | 106370621 A | * 2/2017 | ............ G01N 21/39 |
| CN | 108369137 A | * 8/2018 | ............ G01J 1/0403 |
| EP | 0502717 A1 | | 9/1992 |
| JP | 2004-347327 A2 | | 12/2004 |
| JP | 2009-085887 A2 | | 4/2009 |
| JP | 2012-112663 A2 | | 6/2012 |
| JP | 2013-117454 A2 | | 6/2013 |
| JP | 2015-102545 | | 6/2015 |
| KR | 10-2001-0075299 A | | 11/2001 |

OTHER PUBLICATIONS

Australian Examination Report No. 4, AU Application No. 2018310450, Date of Report Aug. 4, 2021.
Chinese Office Action No. 1, Non-English, Chinese Patent Application No. 201880050176, Date of Office Action Nov. 24, 2021.
Chinese Office Action No. 2, English Translation, Chinese Patent Application No. 201880050176, Date of Office Action Sep. 26, 2022.
Korean Notice of Preliminary Rejection, Non-English, Korean Patent Application No. 10-2020-7002736, Date of Rejection Jun. 23, 2022.
Korean Notice of Preliminary Rejection, English Translation, Korean Patent Application No. 10-2020-7002736, Date of Rejection Jun. 23, 2022.
Japanese Office Action, Non-English, Japanese Patent Application No. 2020-503307, Date of Office Action Mar. 14, 2022.
Japanese Office Action, English Translation, Japanese Patent Application No. 2020-503307, Date of Office Action Mar. 14, 2022.
Rospatent, Russian Office Action and Search Report, Non-English, Russian Patent Application No. 2020103493/28, Date of Office Action Oct. 13, 2020.
Rospatent, Russian Office Action and Search Report, English Translation, Russian Patent Application No. 2020103493/28, Date of Office Action Oct. 13, 2020.

* cited by examiner

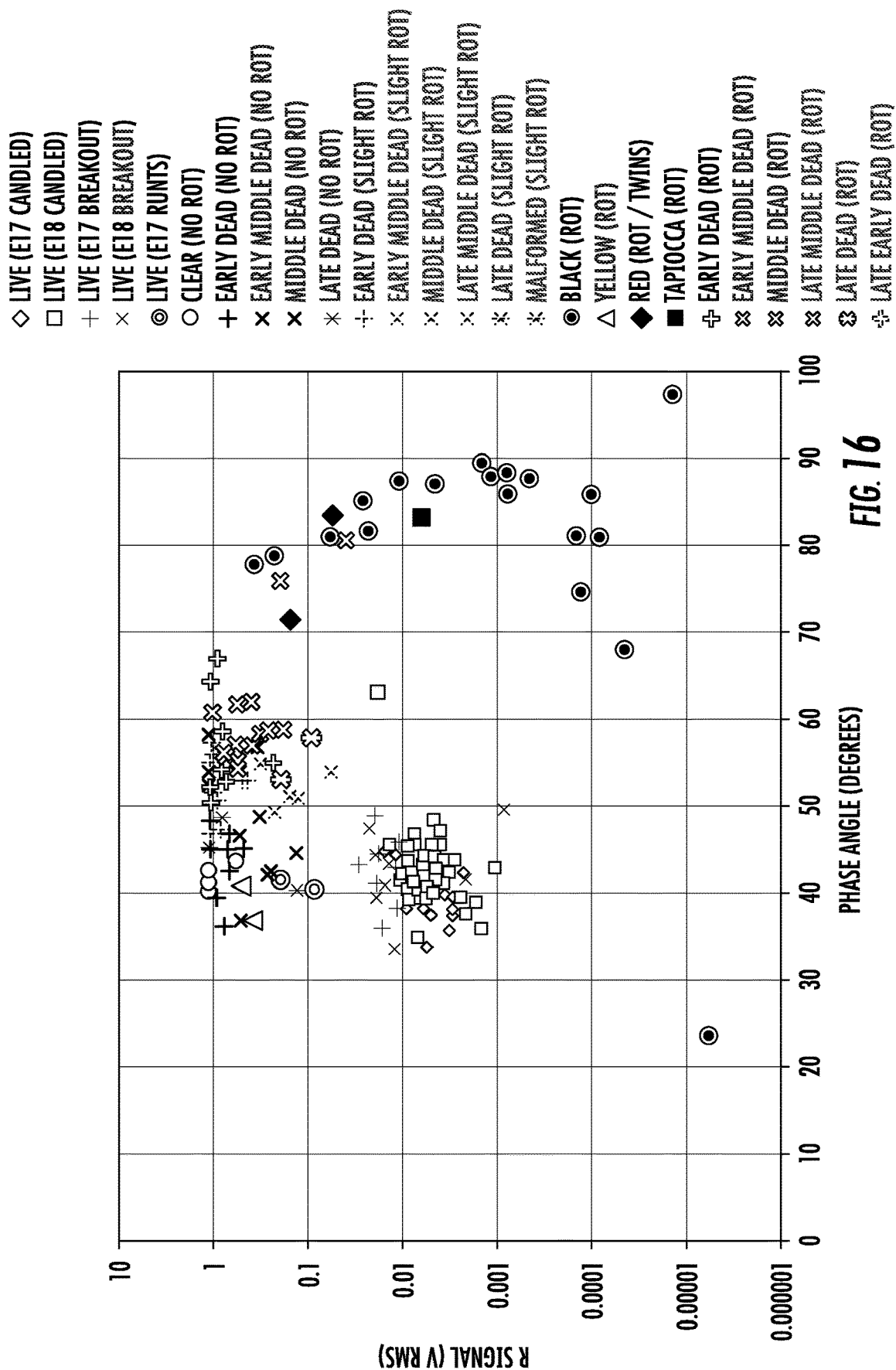

APPARATUS FOR ANALYZING A MEDIA, AND ASSOCIATED EGG IDENTIFICATION APPARATUS AND METHOD

CROSS REFERENCE TO RELATED APPLICATION

This application claims the benefit of U.S. Provisional Patent Application No. 62/539,684, filed Aug. 1, 2017, which is expressly incorporated herein by reference in its entirety.

TECHNICAL FIELD

The present disclosure generally relates to devices for identifying properties of a media to be analyzed. More particularly, the present disclosure relates to an emitter-detector system used to identify properties of a media which in some instances may be used to determine viability or presence of an embryo within an avian egg, and an associated method.

BACKGROUND

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with eggs, although egg shells appear opaque under most lighting conditions, they are in reality somewhat translucent, and when placed in front of direct light, the contents of the egg can be observed.

Eggs which are to be hatched to live poultry are typically candled during embryonic development to identify clear, rotted, and dead eggs (collectively referred to herein as "non-live eggs"). Non-live eggs (also referred to as non-viable eggs) are removed from incubation to increase available incubator space. In many instances it is desirable to introduce a substance, via in ovo injection, into a live egg (also referred to as a viable egg) prior to hatch. Injections of various substances into avian eggs are employed in the commercial poultry industry to decrease post-hatch mortality rates or increase the growth rates of the hatched bird.

In commercial poultry production, only a percentage of commercial broiler eggs hatch. Eggs that do not hatch include eggs that were not fertilized, as well as fertilized eggs that have died. Due to the number of non-live eggs encountered in commercial poultry production, the use of automated methods for in ovo injection, and the cost of treatment substances, an automated method for identifying live eggs (or identifying non-live eggs) and either removing non-live eggs or selectively injecting only live eggs is desirable.

An egg may be a "live" egg, meaning that it has a viable embryo. FIG. 1 illustrates a live poultry egg 1 at about day one of incubation. FIG. 2 illustrates the live egg 1 at about day eleven of incubation. The egg 1 has a somewhat narrow end in the vicinity represented at 10 as well as an oppositely disposed broadened or blunt end portion in the vicinity shown at 20. In FIG. 1, an embryo 2 is represented atop the yolk 3. The egg 1 contains an air cell 4 adjacent the broadened end 20. As illustrated in FIG. 2, the wings 5, legs 6, and beak 7 of a baby chick have developed.

An egg may be a "clear" or "infertile" egg, meaning that it does not have an embryo. More particularly, a "clear" egg is an infertile egg that has not rotted. An egg may be an "early dead" egg, meaning that it has an embryo which died at about one to five days old. An egg may be a "mid-dead" egg, meaning that it has an embryo which died at about five to fifteen days old. An egg may be a "late-dead" egg, meaning that it has an embryo which died at about fifteen to eighteen days old.

An egg may be a "rotted" egg, meaning that the egg includes a rotted infertile yolk (for example, as a result of a crack in the egg's shell) or, alternatively, a rotted, dead embryo. While an "early dead," "mid-dead" or "late-dead egg" may be a rotted egg, those terms as used herein refer to such eggs which have not rotted. Clear, early-dead, mid-dead, late-dead, and rotted eggs may also be categorized as "non-live" eggs because they do not include a living embryo.

Some previous candling apparatuses have employed opacity identification systems in which a plurality of light sources and corresponding light detectors are mounted in an array, and wherein eggs are passed on a flat between the light sources and the light detectors. However, these systems are limited in discriminating among live and non-live eggs, particularly with respect to rotted eggs. Rotted eggs may contain harmful pathogens capable of contaminating otherwise viable eggs proximate thereto.

Accordingly, it would be desirable to provide an egg identification system capable of accurately distinguishing live and non-live eggs, and particularly capable of identifying rotted eggs. Furthermore, it would be desirable to provide an associated method that would facilitate such discrimination of live and non-live eggs in a high throughput and accurate manner.

BRIEF SUMMARY

The above and other needs are met by aspects of the present disclosure which, according to one aspect, provides an apparatus for interrogating a media to be analyzed. The apparatus has an emitter assembly configured to emit light toward a media. The emitter assembly has a first emitter source configured to emit a first light signal and a second emitter source configured to emit a second light signal. The first and second light signals are transmitted through the media in phase quadrature. A detector assembly is configured to detect the first and second light signals transmitted through the media. The detector assembly is further being configured to resolve a relative or absolute amplitude of each of the first and second light signals. A processor is configured to process the detected signal to identify a property of the media using at least one of the relative or absolute amplitudes of the first and second light signals.

Another aspect provides a method of analyzing a media. The method includes transmitting a first light signal and a second light signal in phase quadrature through a media to be analyzed. The method further includes detecting the first and second light signals transmitted through the media, and resolving a relative or absolute amplitude of each of the first and second light signals. The method further includes determining a property of the media using at least one of the relative or absolute amplitudes of the first and second light signals.

Yet another aspect provides an apparatus for non-invasively identifying a present condition of an egg. The apparatus includes an emitter assembly configured to emit light toward an egg. The emitter assembly has a first emitter source configured to emit a first light signal and a second emitter source configured to emit a second light signal. The first and second light signals are transmitted through the egg in phase quadrature. A detector assembly is configured to detect the first and second light signals transmitted through the egg. The detector assembly is further configured to resolve a relative or absolute amplitude of each of the first and second light signals. A processor is configured to process the detected first and second light signals to identify a present condition of the egg using at least one of the relative or absolute amplitudes of the first and second light signals.

Still another aspect provides a method of analyzing a present condition of an egg. The method includes transmitting a first light signal and a second light signal in phase quadrature through an egg to be analyzed. The method further includes detecting the first and second signals transmitted through the egg, and resolving a relative or absolute amplitude of each of the first and second light signals. The method further includes determining a present condition of the egg using at least one of the relative or absolute amplitudes of the first and second light signals.

Thus, various aspects of the present disclosure provide advantages, as otherwise detailed herein.

BRIEF DESCRIPTION OF THE DRAWINGS

Figure 1:
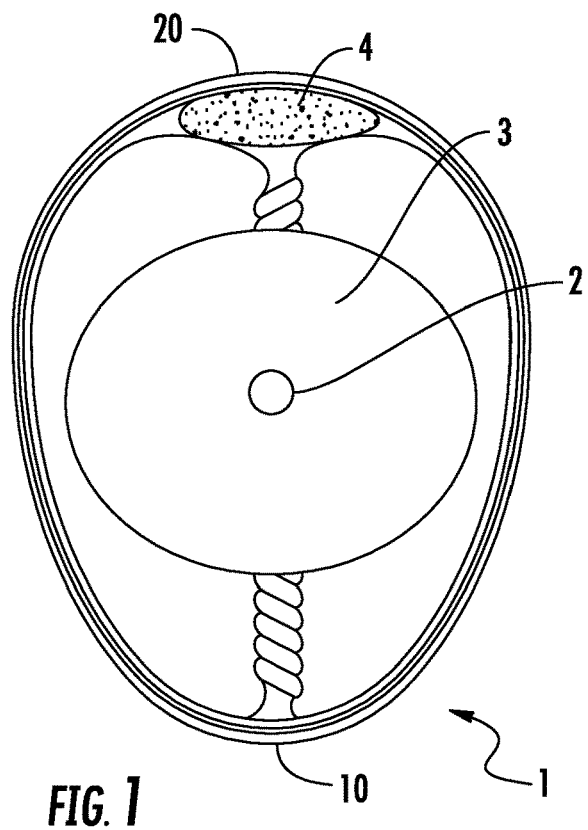
Figure 2:
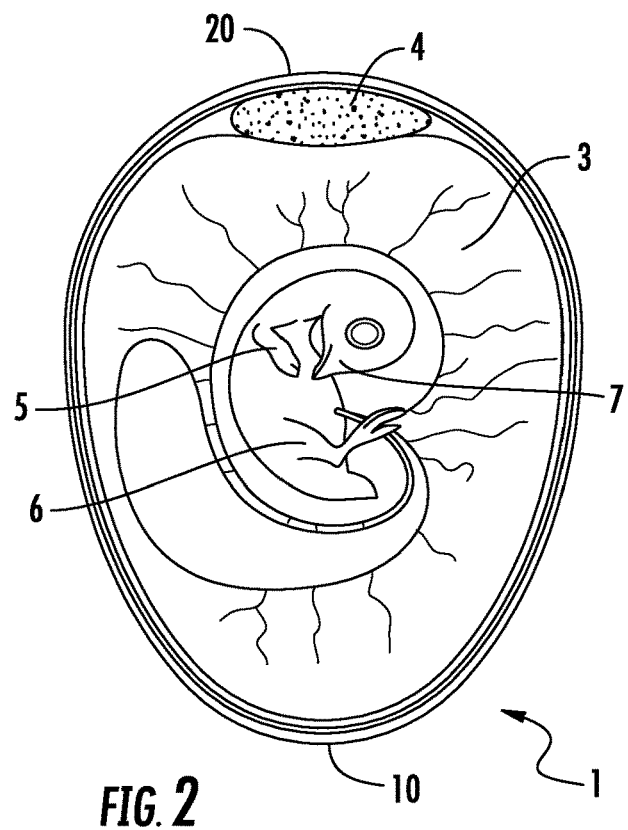
Figure 3:
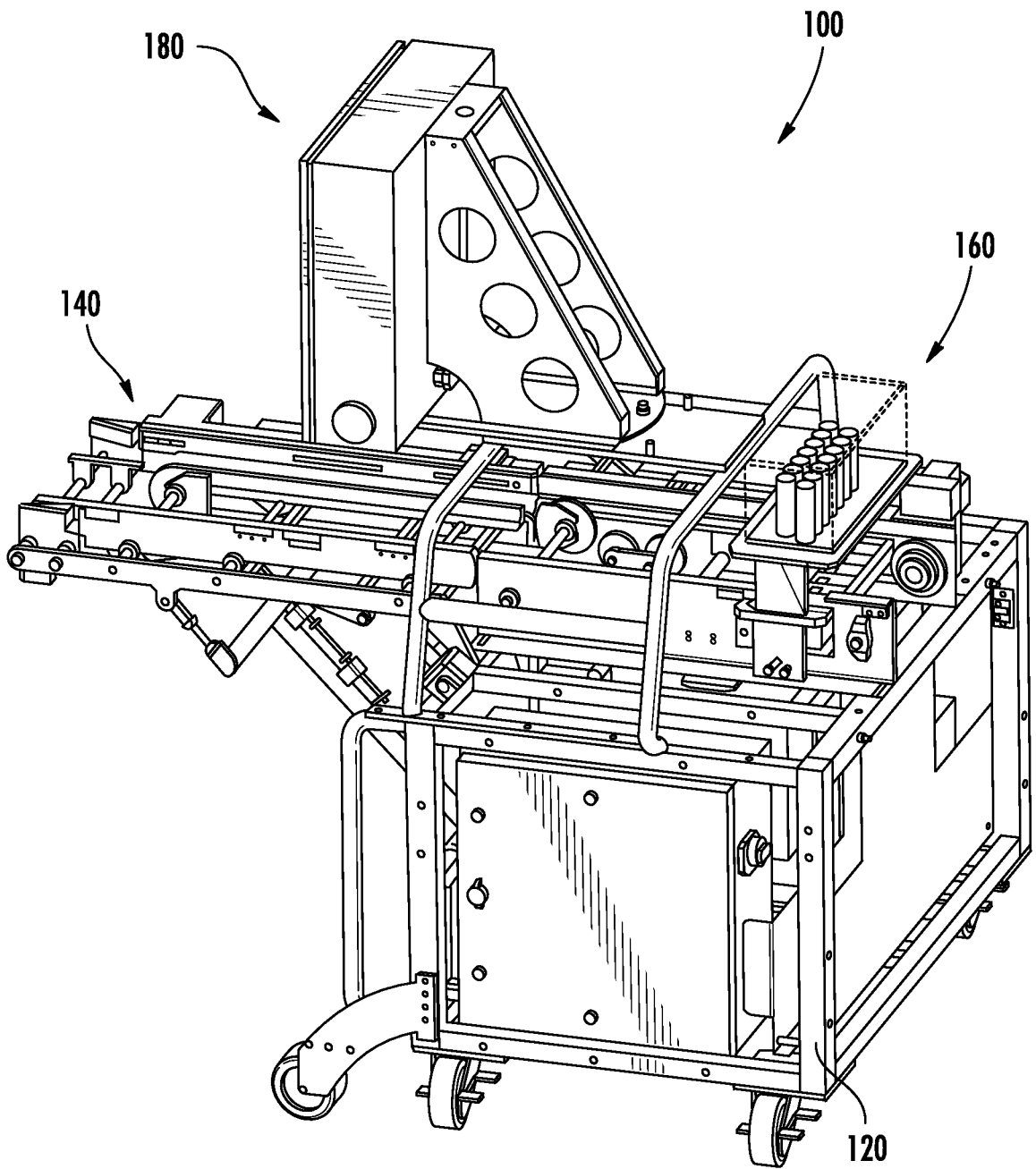
Figure 4:
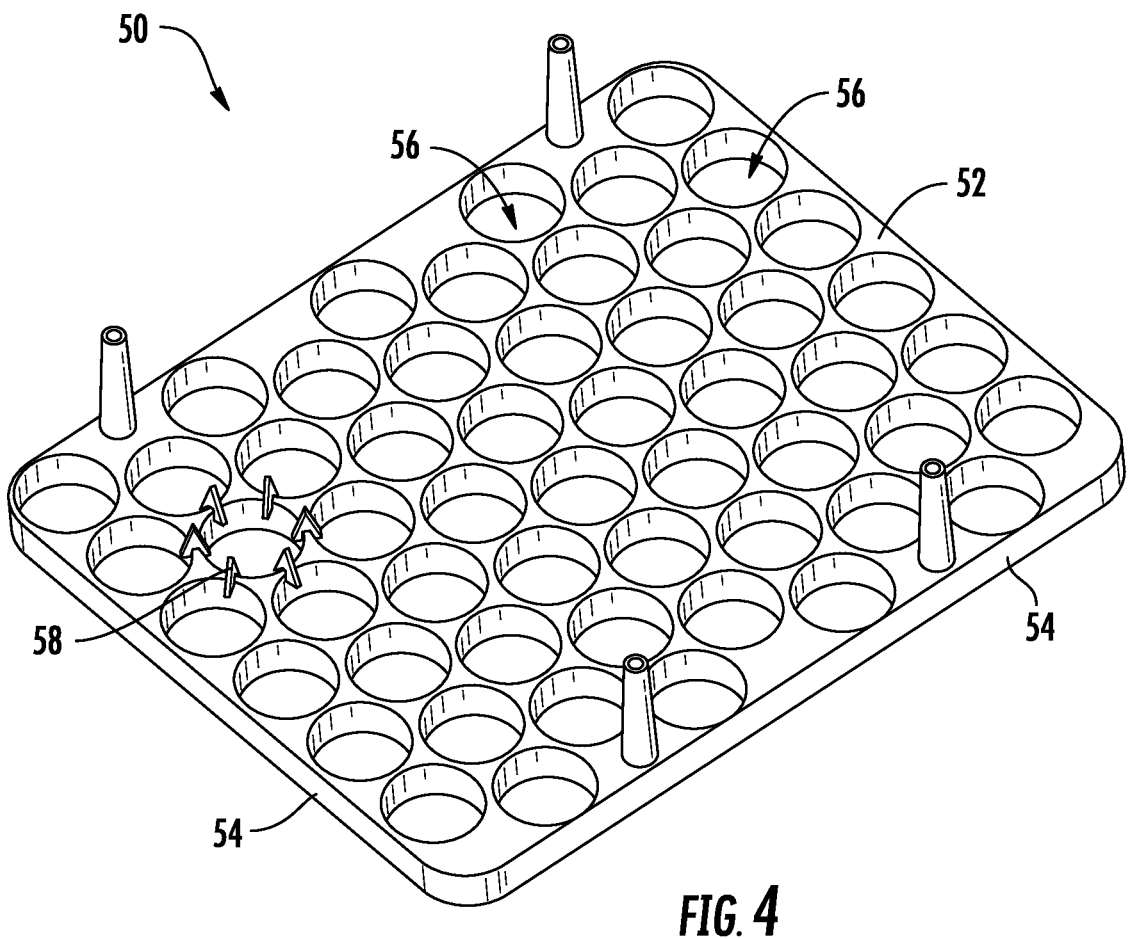
Figure 5:
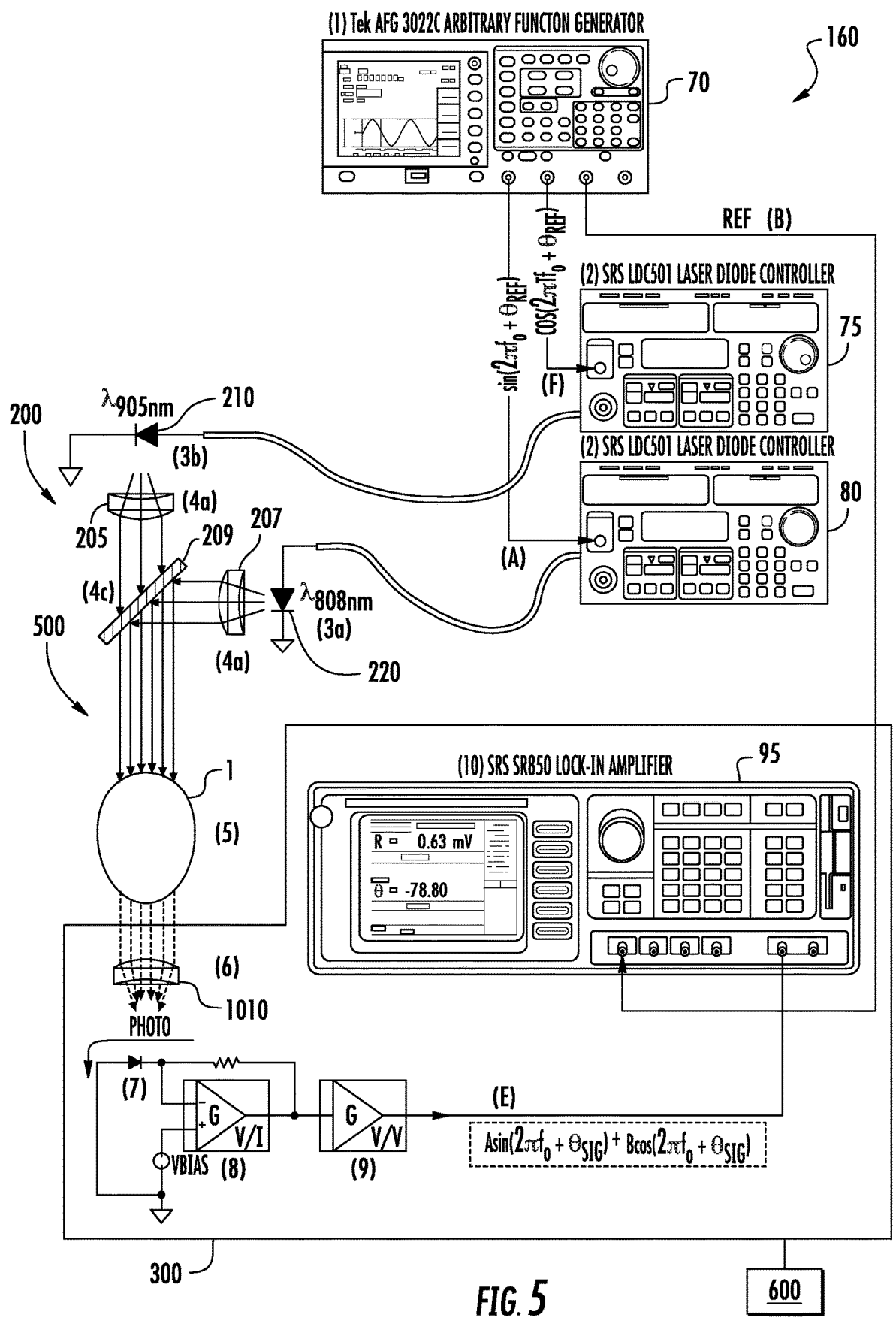
Figure 6:
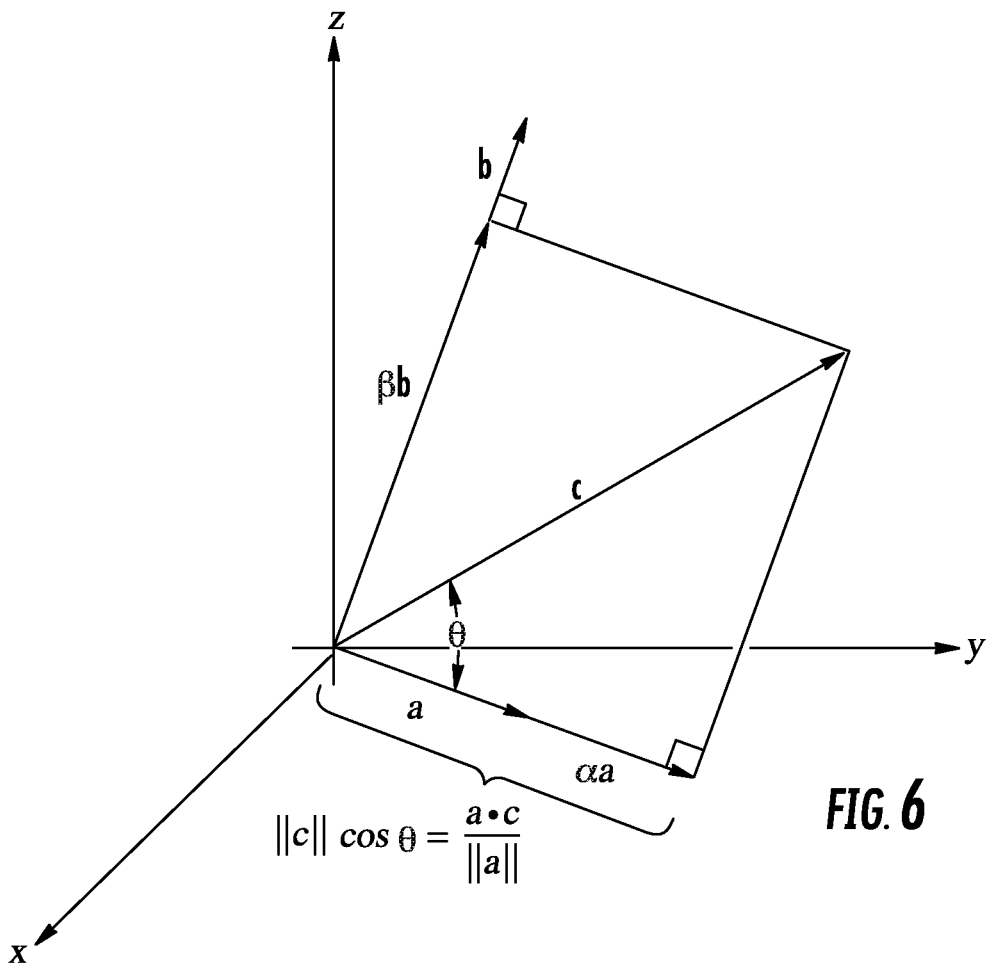
Figure 7:
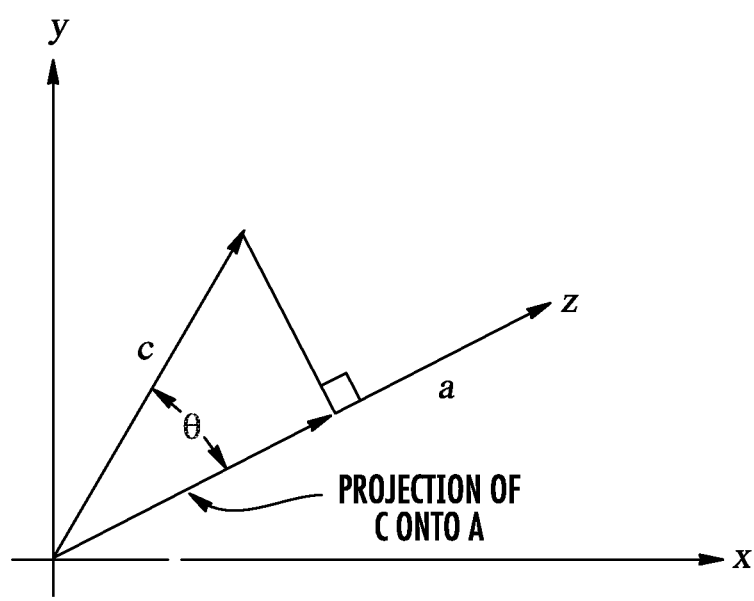
Figure 8:
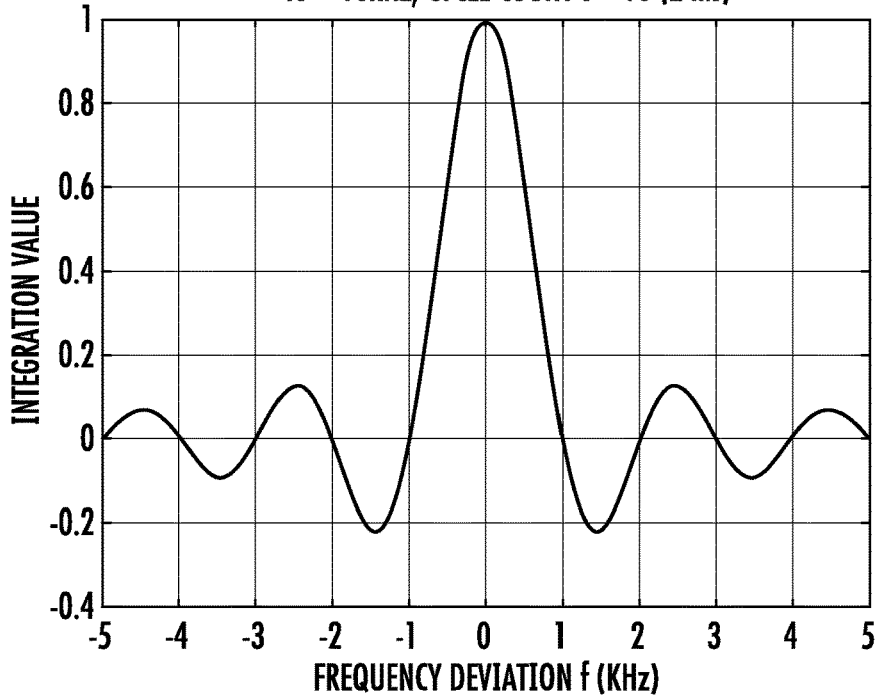
Figure 9:
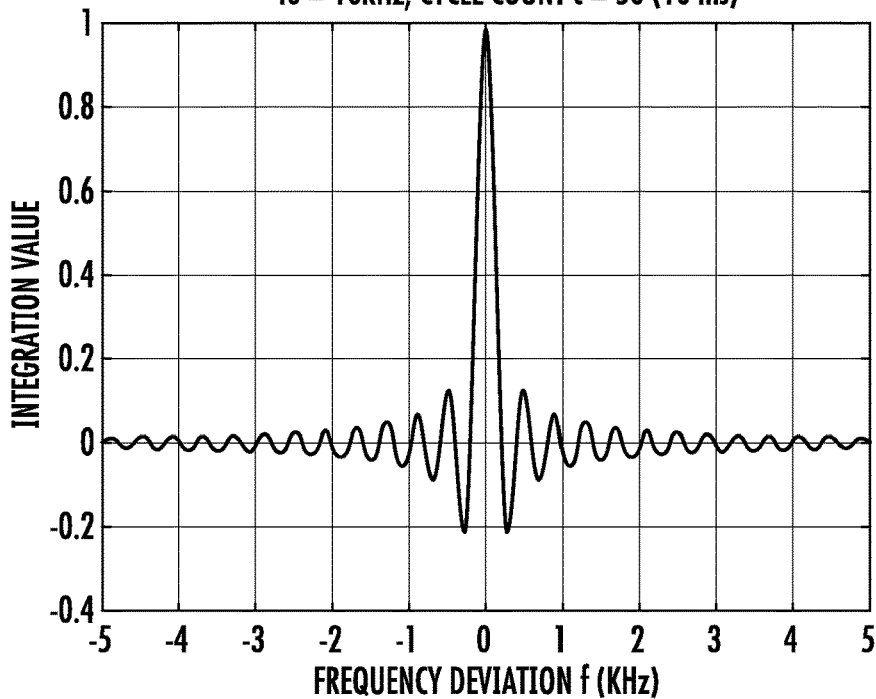
Figure 10:
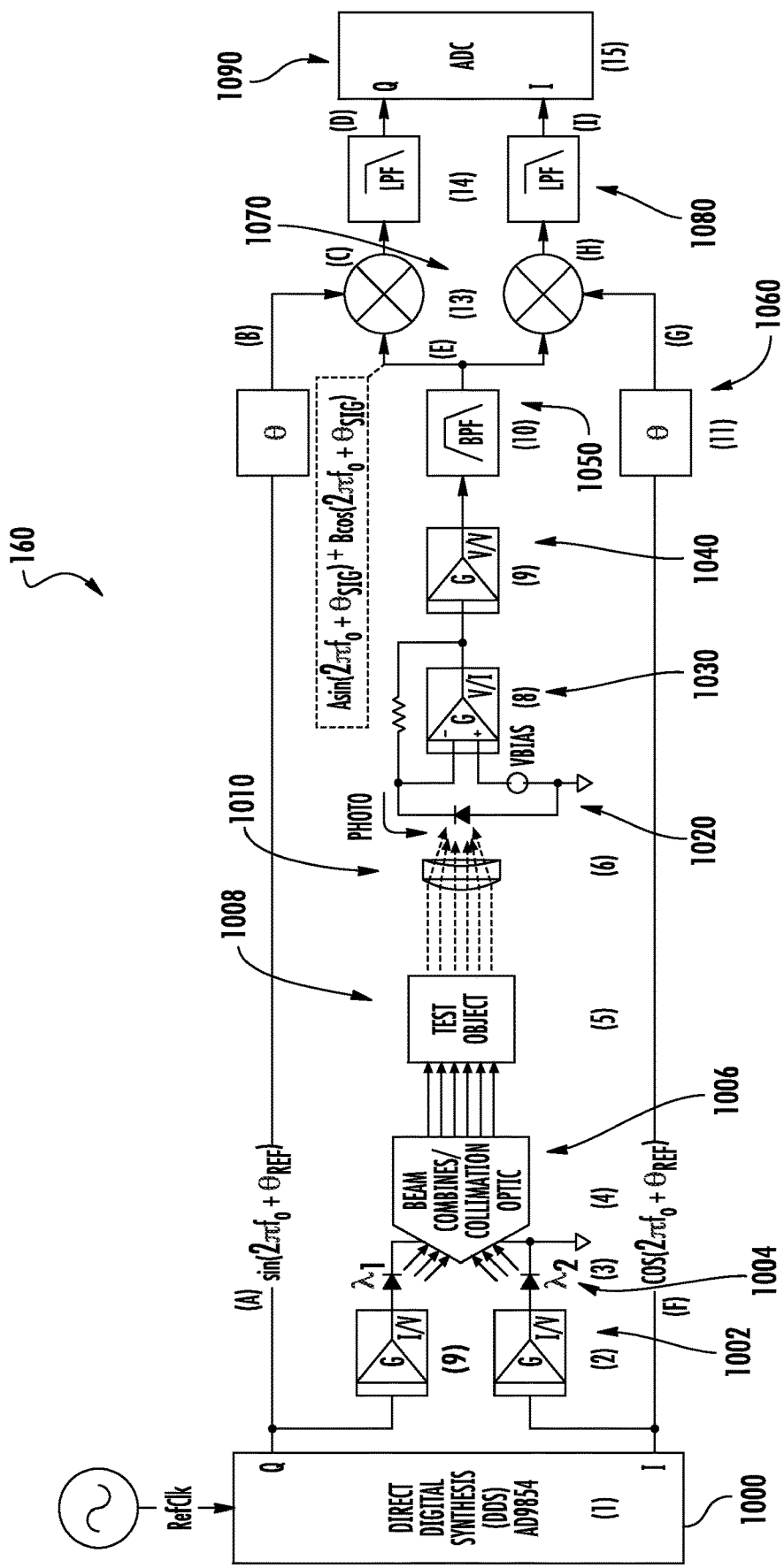
Figure 11:
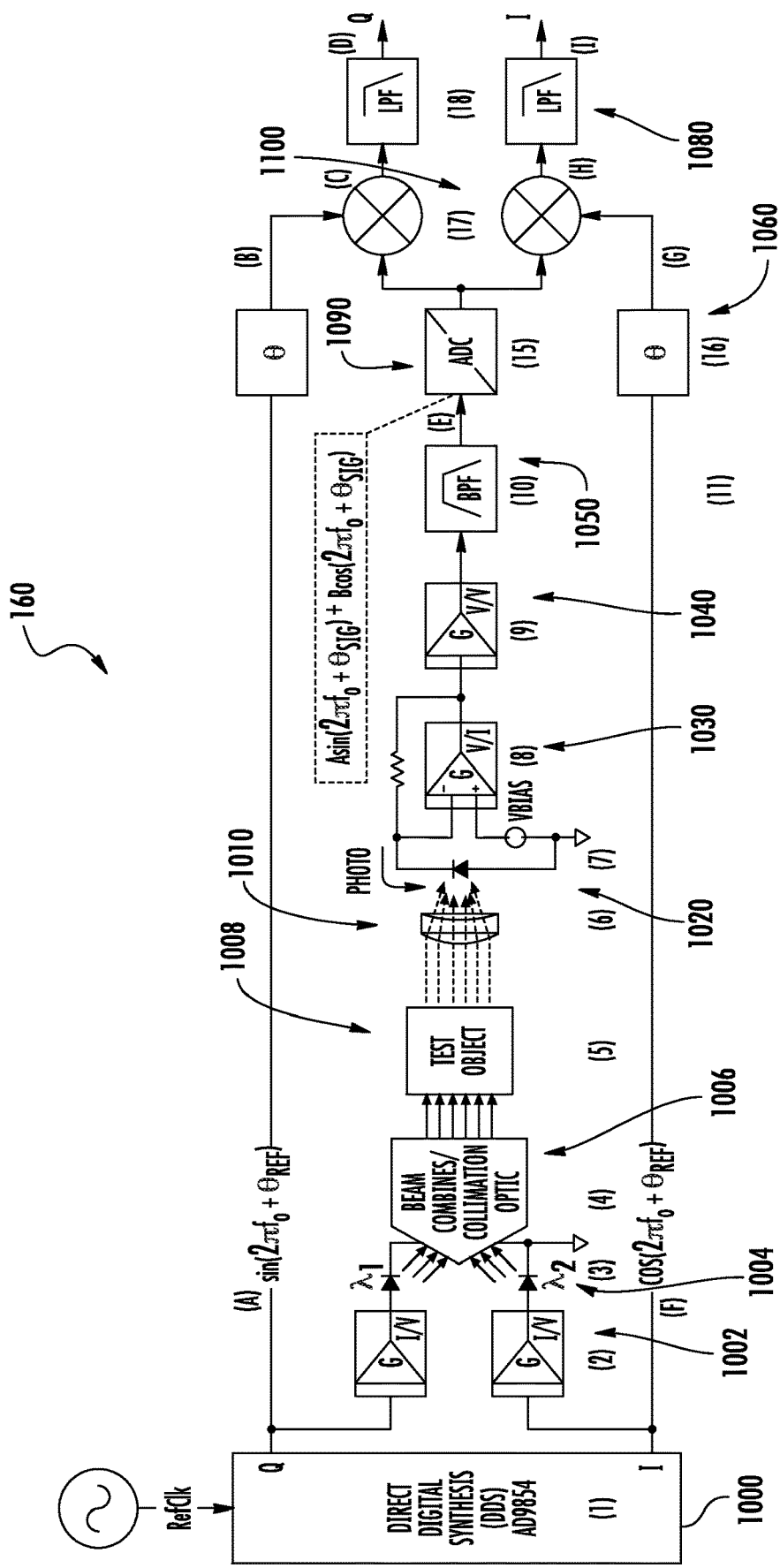
Figure 12:
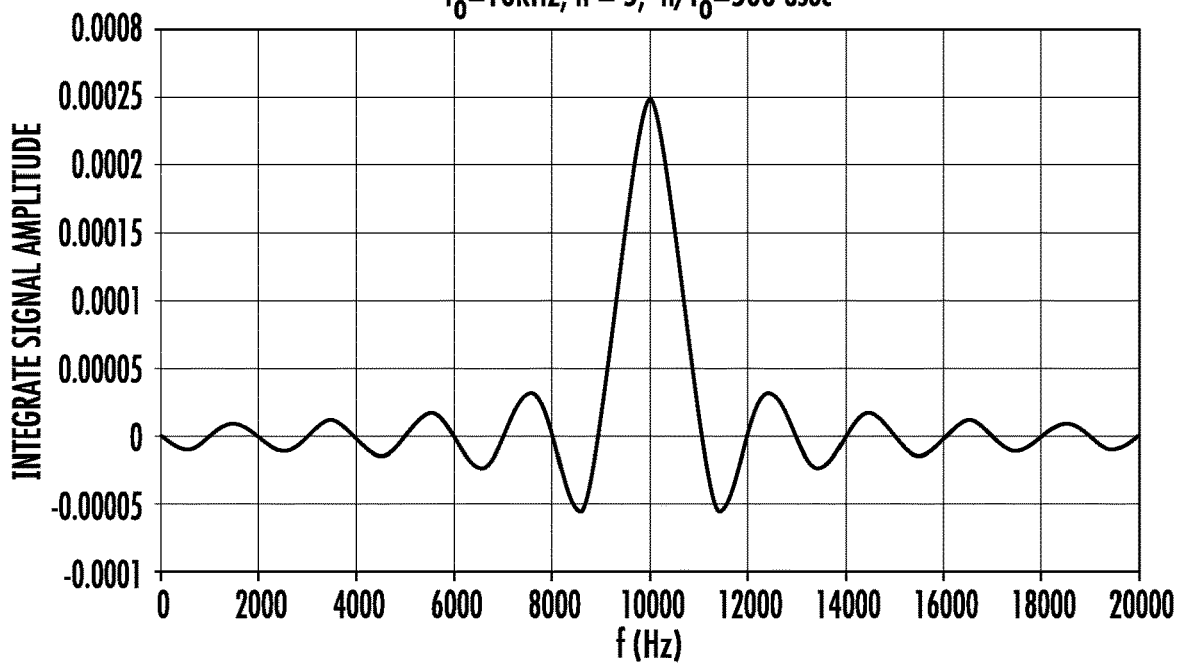
Figure 13:
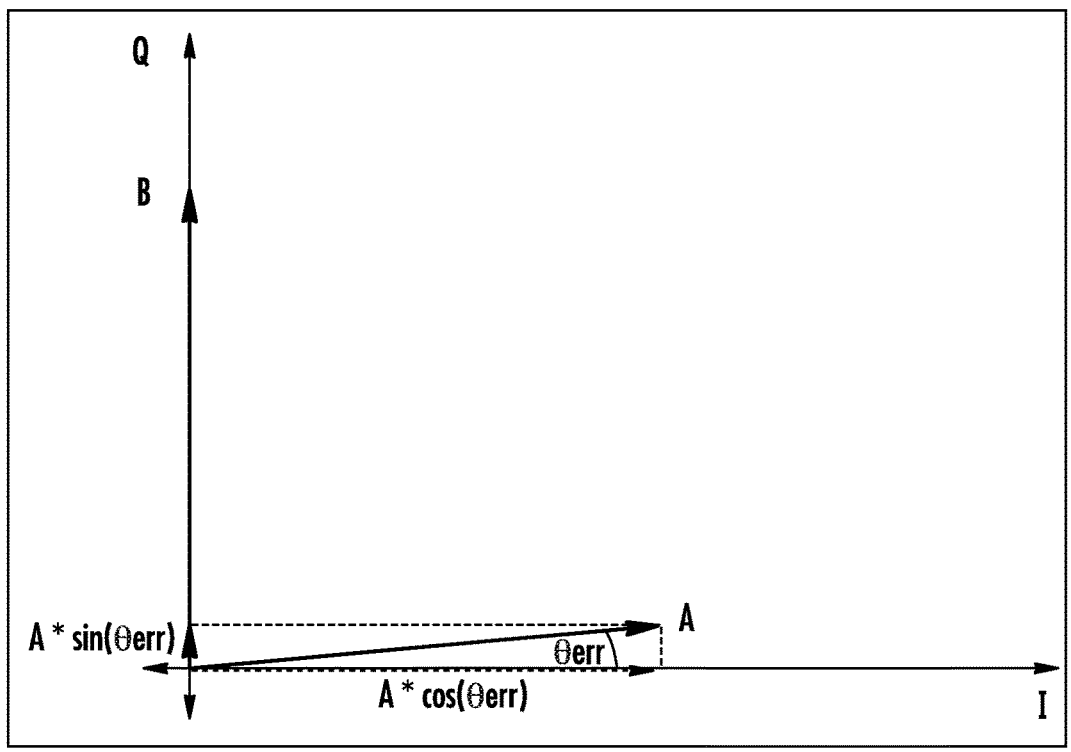
Figure 14:
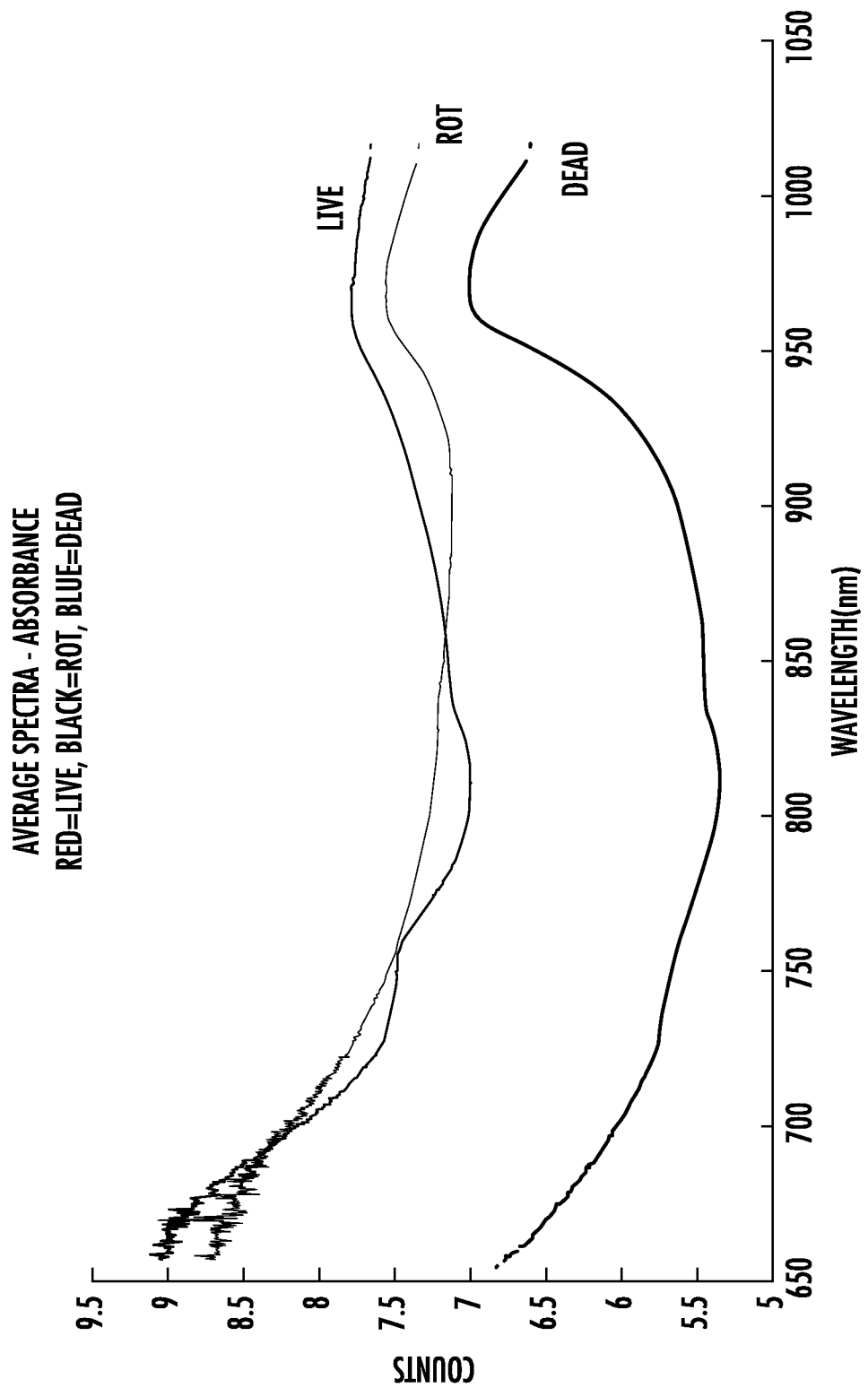
Figure 15:
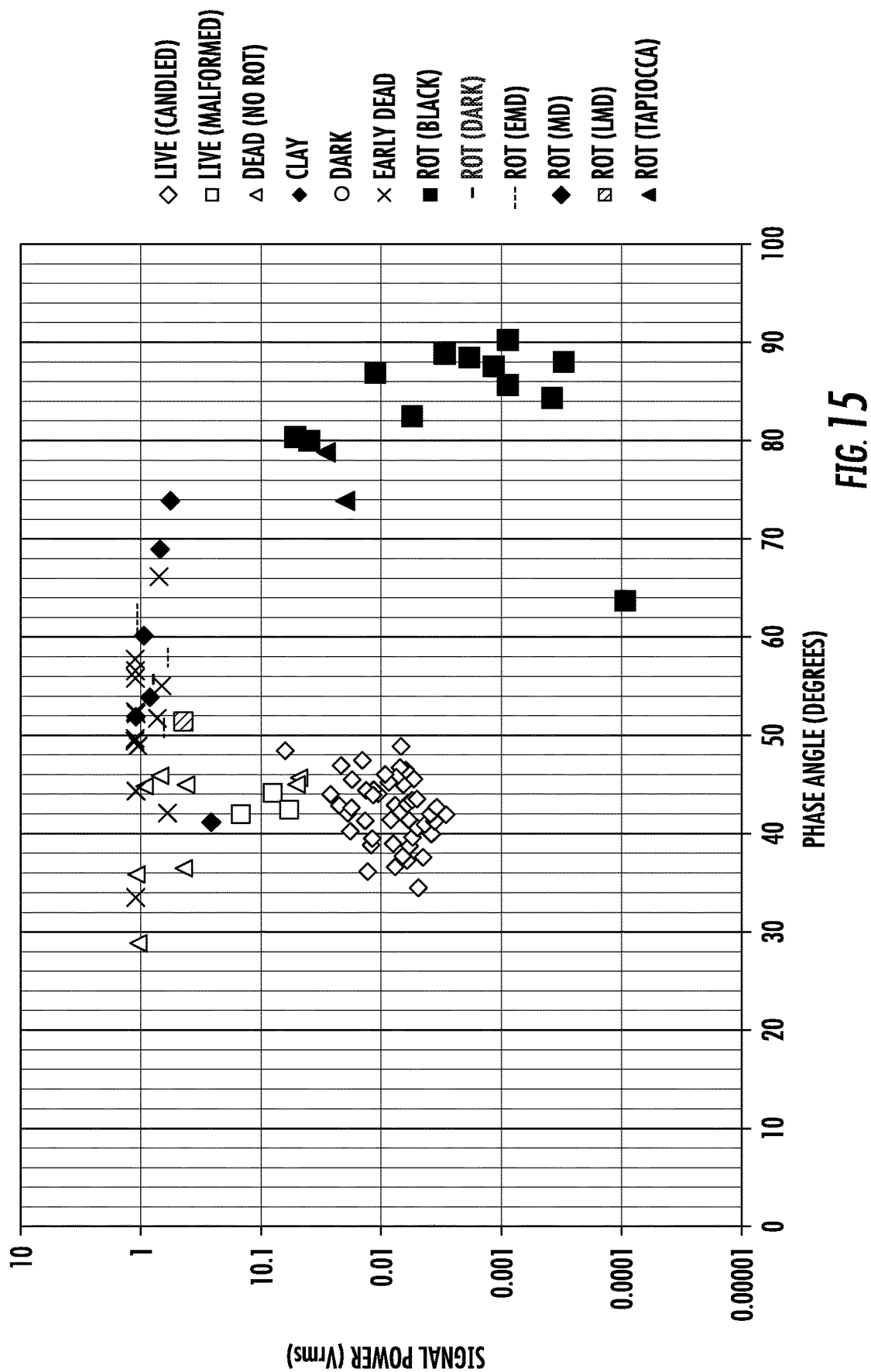
Figure 18:
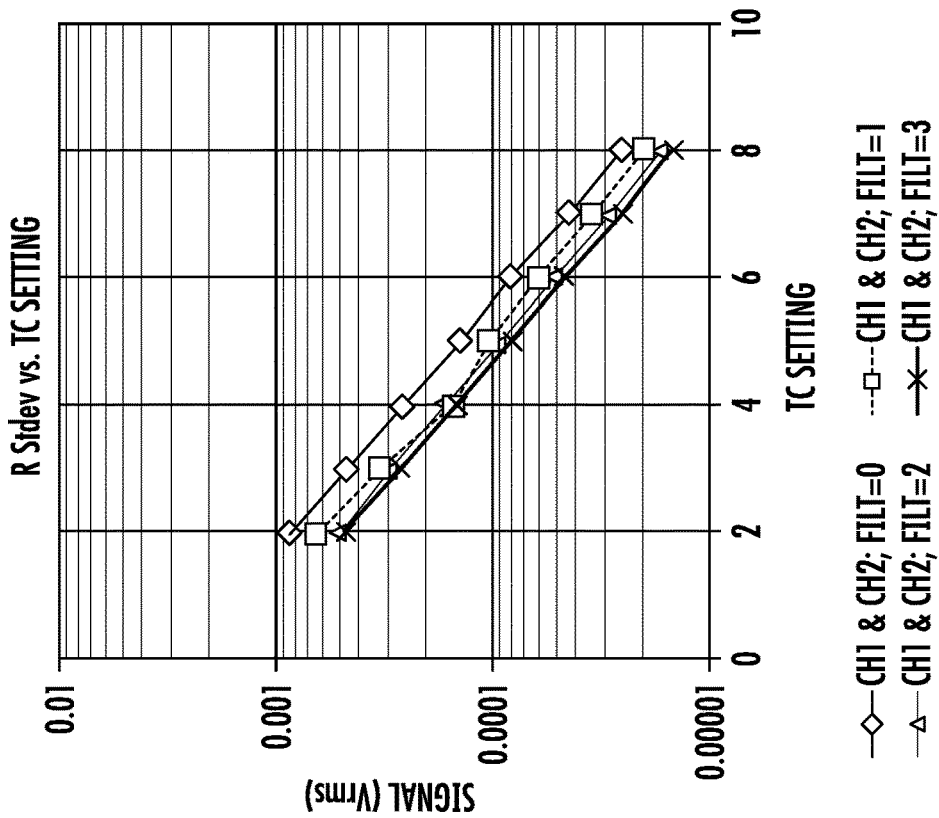
Figure 17:
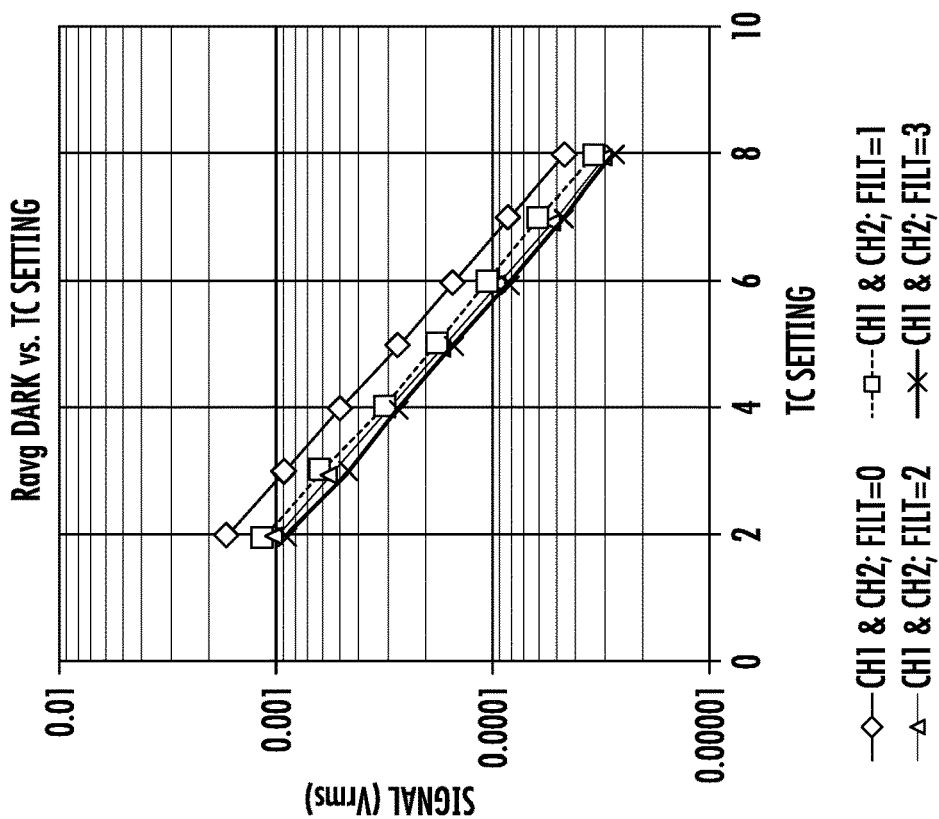

Having thus described various embodiments of the present disclosure in general terms, reference will now be made to the accompanying drawings, which are not necessarily drawn to scale, and wherein:

FIG. 1 illustrates a live chicken egg at about day one of incubation;

FIG. 2 illustrates a live chicken egg at about day eleven of incubation;

FIG. 3 is a perspective schematic view of an egg identification apparatus, according to one aspect of the present disclosure;

FIG. 4 is a perspective schematic view of an egg flat capable of containing eggs in a fixed position;

FIG. 5 illustrates an egg identification system, according to one aspect of the present disclosure;

FIGS. 6 and 7 are graphs illustrating a portion of the egg identification methodology, according to one aspect of the present disclosure;

FIG. 8 is a plot of detector gain vs. the frequency of the power variations of the detected light in accordance with the methodology used for identifying properties of a media, according to one aspect of the present disclosure;

FIG. 9 is a plot of detector gain vs. the frequency of the power variations of the detected light for longer sample times relative to FIG. 8, according to one aspect of the present disclosure;

FIG. 10 illustrates an analog implementation in accordance with the present disclosure;

FIG. 11 illustrates a digital implementation of a down converter in accordance with the present disclosure;

FIG. 12 illustrates methodology aspects of the present disclosure with respect to adjacent channel rejection and frequency planning;

FIG. 13 illustrates the effects of quadrature error as part of the methodology of the present disclosure;

FIG. 14 is a plot of optical density of different egg types versus wavelength of transmitted light;

FIGS. 15 and 16 are graphs plotting signal power versus phase angle for identifying live eggs and non-live eggs, without interfering light;

FIGS. 17 and 18 illustrate the measured relationship between filter bandwidth and the noise floor for the system shown in FIG. 5; and FIGS. 19-22 are graphs plotting signal power versus phase angle for identifying live eggs and non-live eggs, illustrating the effects of self-interfering light.

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

The present disclosure is directed to apparatuses and methods for determining or identifying one or more properties of a media to be analyzed. The present disclosure may have use in pulse oximetry, gas analysis, or other objects or media to be analyzed. More particularly, the present disclosure is directed to apparatuses and methods for improved determination of the viability of an embryo within an egg. In some instances, the present disclosure may be implemented to make a determination of viability of a plurality of eggs in a high throughput manner. In some instances, the eggs may be passed through an identification system in a non-contact or contactless manner, while in other instances the eggs may be contacted by a mechanical light seal to reduce stray signals (e.g., ambient light). As used herein, the terms "non-contact" and "contactless" refer to maintaining a spaced-apart relationship between the egg and certain components of the egg identification system disclosed herein during operation of emitter-detector pairs when determining viability.

Furthermore, the present disclosure is directed to apparatuses and methods using transmission (so-called "through beam") modes for determining viability of an egg. By operating in a transmission mode, the emitter and detector of the egg identification apparatus may be axially aligned along a common longitudinal axis such that the apparatus may be configured in a workable manner. That is, the emitter assembly and the detector assembly may be positioned on opposite sides of the eggs such that the eggs can easily pass therebetween for evaluation and identification.

The methods and apparatuses according to aspects of the present disclosure may be utilized for accurately identifying live and non-live eggs at any time during embryonic development (also referred to as the incubation period). Aspects of the present disclosure are not limited to identification only at a particular day (e.g., day eleven) or time period during the embryonic development period. In addition, methods and apparatus according to aspects of the present disclosure may be used with any types of avian eggs including, but not limited to, chicken, turkey, duck, geese, quail, pheasant eggs, exotic bird eggs, etc.

FIG. 3 illustrates an egg identification apparatus 100 capable of implementing various aspects of the present disclosure. The egg identification apparatus 100 may include a frame 120 and a conveyor system 140 configured to convey a plurality of eggs contained in an egg flat 50 (FIG. 4) to an egg identification system 160. In some instances, the egg identification apparatus 100 may include an operator interface display 180 capable of displaying information related to the egg identification apparatus 100 and/or the eggs passing through the egg identification system 160 for analysis thereof. The egg identification apparatus 100 may include one or more controllers for controlling various aspects of thereof, including the ability to enable and disable certain components of the egg identification system 160. The egg identification apparatus 100 may be portable and, in some instances, may be configured in a modular manner such that it may be connected to other associated devices, such as, for example, an egg injection apparatus, an egg sorting apparatus, an egg transfer apparatus, an egg remover apparatus, or a gender identification apparatus. In some instances, the egg identification system 160 may be directly applied to an egg injection apparatus, an egg sorting apparatus, an egg transfer apparatus, an egg remover apparatus, or a gender identification apparatus.

Referring to FIG. 4, an egg flat 50 may be formed of a body 52 having a plurality of ends 54. The body 52 may define a plurality of open-ended pockets 56, with each pocket 56 capable of receiving an end of a respective egg. In some instances, the narrow end 10 (FIGS. 1 and 2) of the egg may be received within the pocket 56 such that the blunt end 20 projects above the egg flat 50. A plurality of projecting members 58 may be provided about the pockets 56 such that the egg is maintained in a vertical orientation. Although eggs may be carried in egg flats 50, any means of presenting a plurality of eggs over time to the egg identification system 160 for identifying the present condition of eggs may be used.

Referring now to FIG. 5, the egg identification system 160 for non-invasively identifying a present condition of an egg, according to aspects of the present disclosure, is illustrated schematically. The systems and methods described herein may also be referred to as non-invasive in that egg shell structure remains intact throughout the evaluation of the egg. An emitter-detector pair 500 may be provided for use in classifying eggs. The illustrated emitter-detector pair 500 may include an emitter assembly 200 and a detector assembly 300. In operation, a plurality of the emitter-detector pairs 500 may be arranged in an array and utilized to classify a respective array of eggs supported by an egg flat 50 (FIG. 4). The emitter assembly 200 may include an emitter housing. Aspects of the present disclosure are not limited to the illustrated configuration of the emitter housing. The emitter housing may have various shapes, sizes and configurations without limitation. An array of the emitter assemblies 200 may be supported via a frame or other supporting member of the egg identification system 160. Because the egg identification system 160 may be operated in a non-contact manner in which the eggs are not physically contacted thereby, the emitter assemblies 200 may be placed in a stationary position.

An egg 1 may be illuminated with light from first and second emitter sources 210, 220 of the emitter assembly 200 positioned proximate to an egg 1 at the blunt end 20 thereof. In some instances, the light beams from the two emitter sources 210, 220 may be combined and collimated into a single beam represented by a combined signal. In some instances, the light emitted from the light emission sources 210, 220 may be collimated and/or focused. In accordance with various embodiments of the present disclosure, objects may be illuminated with light at wavelengths within the range of between about 400 and 2600 nanometers. For the application of avian eggs, each respective light emission source 210, 220 may particularly illuminate the eggs with light at wavelengths within the visible spectrum, the infrared spectrum, the near-infrared spectrum, or the ultraviolet spectrum. The first and second emitter sources 210, 220 emit light at different wavelengths. The first and second emitter sources 210, 220 may emit light in the range of between about 750-950 nm, and preferably between about 800-910 nm. In some instances, the first emitter source 210 may emit light in the range of about 800-810 nm, and preferably in the range of about 805-809 nm. This region provides high selectivity in avian eggs while providing good transmission characteristics of the first emitter wavelength. The second emitter source may emit light in the range of about 900-910 nm, and preferably in the range of about 905-910 nm. This region also provides high selectivity in avian eggs while providing good transmission characteristics of the second emitter wavelength. Other egg types and materials might require different wavelengths.

The emitter assembly 200 may be configured to maximize emission of the electromagnetic radiation along a longitudinal axis of the egg 1 such that the emissions are coherently directed toward the egg 1. That is, the emitter assembly 200 may be configured to project the emission of the light emission source 210 onto a prescribed region of the egg 1. According to some aspects, the light emitter sources 210, 220 may be formed of, for example, a light emitting diode (LED) or a laser diode (LD), lens, baffles and combining means configured to emit light from various portions of the electromagnetic spectrum. However, aspects of the present disclosure are not limited to the use of LEDs or LDs. Various types of light emitter sources may be utilized without limitation. In particular, any source emitting a narrow spectrum of light may be utilized.

A detector assembly 300 may be positioned adjacent the narrow end 10 of the egg 1, opposite the emitter assembly 200, and may receive light transmitted through the egg. The detector assembly 300 may further include a detection device, such as a photodiode, lenses, baffles, amplifiers and filters. The detector assembly 300 may be configured to measure a targeted portion of the radiant flux transmitted through a media or material as a function of wavelength. With regards to the use of the word "intensity" for light measurements herein, it should be interpreted as "radiant flux" when referring to power measurements (Watts) or "irradiance" for to reference to power/area (W/m^2). The detector assembly 300 may be configured (e.g., via a microprocessor) to convert light intensity values for an egg 1 into useable information for determining the present condition (i.e., viability or non-viability) of an egg. Similarly, the light intensity values may be processed so as to be used in determining whether an egg in question is early dead, middle dead, late dead, clear, cracked, rotted, and/or missing. While the blunt end 20 of the egg 1 is shown and described as being irradiated, it is possible that the positions of the emitter assembly 200 and the detector assembly 300 may be switched such that the electromagnetic radiation is directed upward into the narrow end 10 of the egg 1 and the transmitted light detected at the blunt end 20.

The egg identification system 160 may include one or more controllers or appropriate hardware. For example, the controller(s) 75, 80 may be drivers that control the light emission sources 210, 220. An operator interface (e.g., a display) 180 may be preferably provided to allow an operator to interact with the controller. The controller may be configured to generate control signals to actuate and de-actuate one or more light emission sources 210, 220. A function generator, such as, for example, an arbitrary function generator 70, may be provided to generate electrical waveforms and to control amplitude, frequency and phase. Arbitrary function generators are capable of generating a periodic, user-defined waveform. The controller may also include such other devices as appropriate to control the one or more light emission sources 210, 220 and detector assembly 300, process or otherwise assess and evaluate signals from the detector assembly 300. The controller may include a processor or other suitable programmable or non-programmable circuitry including suitable software.

A processor 600 may be operatively connected to the detector assembly 300 and in some instances may receive and process signals from the detector assembly 300. The processor 600 may also compare a data set generated for an egg with data associated with known egg conditions and, using this comparison data, may classify an egg according to type (i.e., live, clear, dead, rotted). The processor 600 may be configured to: 1) receive and process signals from the detector assembly 300; and 2) process and store data associated with each egg.

The operator interface 180 may be any suitable user interface device and preferably includes a touch screen or keyboard. The operator interface 180 may allow the user to retrieve various information from the controller, to set various parameters and/or to program/reprogram the controller. The operator interface 180 may include other peripheral devices, for example, a printer and a connection to a computer network. The identified conditions of each of a plurality of eggs in a flat 50 may be displayed graphically via the operator interface 180 along with cumulative statistics for a group or flock of eggs. Such cumulative statistics may be assembled, calculated and/or estimated by the processor 600 using the classification data. The cumulative statistics may include, for each group, flock or flat, early dead percentage, mid-dead percentage, and percentage of rotted eggs. These statistics may be useful to monitor and evaluate hatchery and incubator operation, and status and performance of breeds or flocks.

The present disclosure provides novel apparatuses and methods for transmitting two distinct signals on the same sinusoidal carrier, detecting the transmitted signal, and resolving the relative amplitude of each distinct signal at a detector. The combined signal may be transmitted through a media that affects (e.g., attenuates) each signal differently. The interaction of the media with the two signals provides useful information (a signature) about the media. The detected signal, through both relative or absolute amplitude, provides a means to identify properties about the media. The use of dual wavelength on a single carrier is novel in the field of optical absorption measurements. The use of quadrature amplitude modulation (QAM) is a technique used in the field of communications systems for transmitting digital data. Amplitude modulation is applied by absorption in the measured media rather than by a transmitter. The absorption of the two wavelengths varies the detected signal amplitude differently depending on the media. This is simplified in that there is no phase shift keying (single quadrant) and no amplitude shift keying (smooth transitions). This novel method provides highly accurate relative absorption measurements that may be used for identifying properties of a media.

By transmitting the two signals in phase quadrature (i.e., at 90 degree phase), the orthogonal properties of the two signals enables the amplitude of each signal to be recovered with high accuracy knowing the phase of each signal. To calibrate the signals, the phase of either signal may be readily measured by enabling only the signal of interest and measuring the phase of the received signal relative to the reference signal used to generate the transmitted signal. As such, the reference phase of the first signal may be determined and the drive signal to the second signal compensated to bring the two signals into phase quadrature at the detector.

This technique is advantageous in discriminating small changes in amplitudes between the two signals since the path gain or attenuation is the same for both signals. Further, since the signals may be transmitted at the same frequency, frequency dependent variations in the signal processing, such as filter response, affect both signals identically.

In this regard, the present disclosure provides a first periodic signal and a second periodic signal transmitted in a media with a 90 degree phase offset. The combined signal may be transmitted through a media that interacts with the first periodic signal and the second periodic signal differently. The media may attenuate each of these signals. The signal exiting the media may have useful information about the material properties in the amplitudes of the first periodic signal and the second periodic signal. In the case of light signals, the photodetector output amplitude is the difference between the maximum and minimum detected radiant flux (flux meaning that which strikes the photodector). Knowing the original phase of the first periodic signal and/or the second periodic signal, the amplitudes of each signal may be determined.

In some instances, the first periodic signal and the second periodic signal may be light emitted at different wavelengths. The light signals may be detected by a photodetector positioned opposite a light emitting source. The media may be any material where the transmission of light at different wavelengths through the media reveals a property thereof. In some instances, the media may be an avian egg such as a chicken egg.

As mentioned previously, the first and second periodic signal may be transmitted in phase quadrature with a 90 degree phase offset. In vector analysis, the inner product enables the angle subtended by two vectors to be determined, as follows:

$$a \cdot b = \|a\| \|b\| \cos(\Theta)$$

For example, if a and b are nonzero vectors in a three dimensional space R3 and $\Theta$ is the angle between them, then $a \cdot b = 0$ if and only if $\cos(\Theta) = 0$. This has a useful physical interpretation in that two vectors are perpendicular if the inner product evaluate to zero. Hence, the inner product provides a convenient method for determining if two vectors are perpendicular or orthogonal. Vectors with a norm (length) of 1 are called unit vectors. Unit vectors are said to be normalized. If a group of vectors are mutually orthogonal and normalized, the system is said to be orthonormal. An orthonormal vector set forms a reference system. The x-y plane in a Cartesian coordinate system, the real-imaginary plane describing complex variables, and the i-j-k vectors describing a three-dimensional system are examples of orthonormal basis vector sets defining familiar reference systems.

Further, referring to FIGS. 6 and 7, the inner product provides a measure of how a vector c "projects" onto another vector a. Assume that a is a non-zero unit vector where $\|a\|=1$. Assume that b is a second non-zero unit vector where $\|b\|=1$ and b is orthogonal to a, where $a \cdot b = 0$. The vector c may be described as $c = \alpha a + \beta b$ where $\alpha$ and $\beta$ are scalars. The product $\alpha a$ is called the component of c along a, or the projection of c along a:

$$a \cdot c = a(\alpha a + \beta b) = \alpha a \cdot a + \beta a \cdot b \text{ (note: } a \cdot b = 0\text{)}$$

$$\alpha = (a \cdot c)/(a \cdot a) = (\|a\| \|c\| \cos(\Theta))/(\|a\| \|a\| \cos(0)) \text{(note: } \|a\|=1\text{)}$$

$$\alpha = a \cdot c = \|c\| \cos(\Theta)$$

In the development of the Fourier series, the concept of orthogonality of vectors is generalized to functions. The standard inner product of two real-valued functions u(x) and v(x) on the interval $\alpha \leq x \leq \beta$ is defined by $$(u,v) = \int_\alpha^\beta u(x)v(x)dx$$

The functions u and v are said to be orthogonal on $\alpha \leq x \leq \beta$ if their inner product vanishes; that is, if $$\int_\alpha^\beta u(x)v(x)dx = 0$$

A set of functions is said to be mutually orthogonal if each distinct pair of function in the set is orthogonal. The following theorem relates these concepts to the functions sin (mπx/l) and cos (mπx/l). The functions sin (mπx/l) and cos (mπx/l), m=1, 2, . . . , form a mutually orthogonal set of functions on the interval –l≤x≤l. They satisfy the following equations, known as orthogonality relations:

$$\int_{-l}^{l} \cos\frac{m\pi x}{l} \cos\frac{n\pi x}{l} dx = \begin{cases} 0, & m \neq n, \\ l, & m = n; \end{cases} \quad (1)$$

$$\int_{-l}^{l} \cos\frac{m\pi x}{l} \sin\frac{n\pi x}{l} dx = 0, \text{ all } m, n; \quad (2)$$

$$\int_{-l}^{l} \sin\frac{m\pi x}{l} \sin\frac{n\pi x}{l} dx = \begin{cases} 0, & m \neq n, \\ l, & m = n. \end{cases} \quad (3)$$

The relationships in Equation (1), (2) and (3) may be referred to as being orthogonal in frequency when m !=n, while the relationship in Equation (2) may be referred to as being orthogonal in phase when m=n. Two signals that are orthogonal in frequency may be used in the implementation of the disclosed apparatuses and methods. Alternatively, two signals that are orthogonal in phase may be used in the implementation of the disclosed apparatuses and methods.

Like their vector counterparts, a mutually orthogonal set of functions may form a reference system to describe other functions. For example, the Fourier series using sine, cosine, or complex exponentials may be used to describe any periodic function.

These results may be obtained by direct integration. For example, $$\int_{-l}^{l} \sin\frac{m\pi x}{l} \sin\frac{n\pi x}{l} dx = \frac{1}{2}\int_{-l}^{l}\left[\cos\frac{(m-n)\pi x}{l} - \cos\frac{(m+n)\pi x}{l}\right]dx$$

$$= \frac{1}{2}\frac{l}{\pi}\left\{\frac{\sin[(m-n)\pi x/l]}{m-n} - \frac{\sin[(m+n)\pi x/l]}{m+n}\right\}\Big|_{-l}^{l}$$

$$= 0,$$

as long as m+n and m−n are not zero. Since m and n are positive, m+n≠0. On the other hand, if m−n=0, then m=n, and the integral must be evaluated in a different way. In this case $$\int_{-l}^{l} \sin\frac{m\pi x}{l} \sin\frac{n\pi x}{l} dx = \frac{1}{2}\int_{-l}^{l}\left(\sin\frac{m\pi x}{l}\right)^2 dx$$

$$= \frac{1}{2}\frac{l}{\pi}\left[1 - \cos\frac{2m\pi x}{l}\right]ds$$

$$= \frac{1}{2}\left\{x - \frac{\sin(2m\pi n/l)}{2m\pi/l}\right\}\Big|_{-l}^{l}$$

$$= L$$

In Equations (1) and (3) above, it is noted that the integration value when m=n is a function of the integration time. That is the "strength" of the recovered "signal" increases with integration time. In Equations (1), (2) and (3) above, it is noted that the frequencies are integer multiples of 1/(2l), otherwise there is a residual error term. It is further noted that in the results of the direct integration where m≠n, the second term is small compared to the first term for large values of m and/or n. Conversely, the first terms become large in the region where m and n approach the same value.

In Equations (1)-(3) above, let:

$$m = cf/f_o$$

$$n = cf_o/f_o = c$$

$$l = c/(2f_o)$$

$$x = t$$

Where:
$f_o$=the desired detection frequency
c=an integer number of cycles of $f_o$ in l. Note that the integration time is 2l.
t=time
Consider the following example where $f_o$=10 kHz, c=10 cycles or 2 ms.

$$m = 10f/10000 = f/1000$$

$$n = 10$$

$$l = 10/(2*10000) = 0.0005$$

In some instances, a plurality of emitter-detector pairs may be implemented so as to increase throughput with respect to eggs moving through the egg identification apparatus 100. Accordingly to aspects of the present disclosure, the emitters in such an arrangement may transmit signals having orthogonal frequency relationships in accordance with a frequency planning scheme.

Detector gain versus frequency is plotted in FIG. 8. It is noted that a null occurs and zero signal is detected when m is an integer value (i.e., f/1000 is an integer). This may be useful in frequency planning allowing a plurality of emitters transmitting at different frequencies. By controlling the integration time or data sampling (acquisition size and period), a detector may be made highly insensitive to adjacent transmitters emitting on these frequency nulls. In this example, the detector is insensitive to adjacent signals set on 1,000 Hz boundaries (excluding $f_o$=10,000 Hz detection frequency). However, when m is not an integer, there is a residual gain term that is to be considered in the detected signal.

FIG. 9 shows how gain is affected by setting c=50 cycles or 10 ms. Although the ratio of the signal gain of the desired frequency at $f_o$ to the gain in the first "lobe" remains the same, the maximum gain in each lobe is pulled in closer to $f_o$. For example, the consequences of a 12.5 kHz interferer are much more severe in the c=10/1 ms case than in the c=50/10 ms case. With increasing integration time, the gain in these lobes becomes less important. In addition, the number of cancellation frequencies increases with integration time allowing for a denser frequency plan (i.e., more nulls are available to place the adjacent channel).

Signal processing of the present disclosure may be performed using a phase-sensitive detector, e.g., a lock-in amplifier such as products SR510/SR530, SR810/SR830, and SR850, all available from Stanford Research Systems. A lock-in amplifier is a type of amplifier that can extract a signal with a known carrier wave from an extremely noisy environment. Such lock-in amplifiers may be used for performing down conversion multiplication in the digital domain. Following an analog gain block and anti-aliasing stage, these systems may immediately perform analog-to-digital conversion (ADC).

Lock-in measurements require a frequency reference. Typically, the object under test is excited by the reference signal:

$$V_{REF} * \sin(2\pi f_0 t + \theta_{REF})$$

where:
$V_{REF}$=the amplitude of the reference
$f_0$=the frequency of the reference in Hertz
t=the time in seconds
$\theta_{REF}$=the phase of the reference signal in radians.

Without loss of generality, $V_{REF}$ may be assumed to be unity. All subsequent amplitudes may then be considered relative to the reference signal. The detector amplifies the signal from the system. The output from this amplification process is represented by:

$$V_{SIG} * \sin(2\pi f t + \theta_{SIG})$$

where:
$V_{SIG}$=the amplitude of the output signal
f=the frequency of the output signal in Hertz
t=the time in seconds
$\theta_{REF}$=the phase of the reference signal in radians.

It is noted that $V_{SIG} \ll V_{REF}$ in typical lock-in applications. The detector may multiply the amplified signal by the original reference signal. The multiplication may be phase sensitive and may be performed in either a digital or analog domain. The output of the power spectral density (PSD) is the product of two sine waves:

$$V_{PSD} = V_{SIG} * \sin(2\pi f t + \theta_{SIG}) * \sin(2\pi f_0 t + \theta_{REF}) \text{ NOTE: Assume } V_{REF} = 1$$
$$= 1/2 V_{SIG} * \cos(2\pi[f - f_0]t + \theta_{SIG} - \theta_{REF}) - 1/2 V_{SIG} *$$
$$\cos(2\pi[f + f_0]t + \theta_{SIG} + \theta_{REF})$$

For a given input frequency, PSD output is two AC signals, one at the difference frequency ($f_0$–f) and the other at the sum frequency ($f_0$+f). If the PSD output is passed through a low pass filter, the AC sum term ($f_0$+f) is removed, leaving the difference term:

$$=1/2 V_{SIG} * \cos(2\pi[f-f_0]t + \theta_{SIG} - \theta_{REF})$$

When f=$f_0$, a DC signal results in the PSD:

$$V_{PSD} = 1/2 V_{SIG} * \cos(\theta_{SIG} - \theta_{REF})$$

This last equation demonstrates the need for the phase between the signals, $\theta_{SIG} - \theta_{REF}$, to be time invariant. Otherwise, $\cos(\theta_{SIG} - \theta_{REF})$ will change and $V_{PSD}$ will not strictly be a DC signal. In other words, the detector reference may be phase-locked to the signal reference. By adjusting $\theta_{REF}$ to $\theta_{SIG}$, $\theta_{SIG} - \theta_{REF}$ may be made equal to zero and $\cos(\theta_{SIG} - \theta_{REF})=1$. This adjustment may be made with a phase adjustment $\theta = \theta_{SIG} - \theta_{REF}$ prior to the mixer resulting in:

$$V_{PSD} = 1/2 V_{SIG}$$

Conversely, by adjusting $\theta_{REF}$ to $\theta_{SIG}$–90°, ($\theta_{SIG} - \theta_{REF}$) may be made equal to 90. In this case $\cos(\theta_{SIG} - \theta_{REF})=0$ and the input signal is cancelled. Typically, in lock-in amplifier applications, this phase dependency may be eliminated by adding a second PSD. If the second PSD multiplies the signal with the reference oscillator shifted by 90°, i.e. the reference signal $\sin(2\pi f_0 t + 90 + \theta_{REF}) = \cos(2\pi f_0 t + \theta_{REF})$ its low pass filtered output will be:

$$V_{PSD2} = 1/2 V_{SIG} * \sin(\theta_{SIG} - \theta_{REF})$$

Now, there are two outputs: one proportional to cos θ and the other proportional to sin θ. Calling the first output I and the second Q, $$I = 1/2 V_{SIG} * \cos \theta$$

$$Q = 1/2 V_{SIG} * \sin \theta$$

These two quantities represent the signal as a vector relative to the lock-in reference oscillator. "I" is called the 'in-phase' component and "Q" the 'quadrature' component. Typically, a lock-in amplifier uses the second PSD to calculate the phase difference between the output and the input signal in addition to removing the phase dependence from the magnitude calculation as follows:

$$R = (I^2 + Q^2)^{1/2} V_{SIG}$$

$$\theta = \tan^{-1}(Q/I)$$

Phase-sensitive detection provided by the lock-in amplifier may be applied to optical multispectral measurements such as pulse oximetery to enable two wavelengths to be measured on a single reference frequency $f_0$. This technique enables in a simple ratiometric comparison to be made between the detected power of the two signals at wavelengths $\lambda_1$ and $\lambda_2$.

The orthogonal rejection properties of the system may be used to transmit and detect two signals on the same frequency, provided:
i) the two signals are 90° out-of-phase (e.g. they are orthogonal in phase), and
ii) The phase difference between the two signals and the reference is known.

As used herein, the term "reference frequency" is used interchangeably with "channel." Conceptually, power measurements for individual wavelength may be differentiated at a detector by their frequency. Two wavelengths may be further differentiated within a reference frequency or channel by their phase.

An analog implementation in accordance with the present disclosure is shown in FIG. 10. Quadrature reference clocks $$\sin(2\pi f_0 t + \theta_{REF}) \text{ and} \quad (A)$$

$$\cos(2\pi f_0 t + \theta_{REF}) \quad (F)$$

may be generated using direct digital synthesis (DDS) 1000. These two references have arbitrary absolute phase $\theta_{REF}$ but have a relative phase to each other of 90°. A representative device capable of generating the required signals is the product AD9854, available from Analog Devices, or an AFG3022C Arbitrary Function Generator (AFG), available from Tektronics. It is noted that there are other methods for generating quadrature references (e.g. a phase-locked loop w/digital division). Other methods for generating the quadrature reference may be used without changing the nature of the measurement system.

The reference signal (A) and (F) are used to make faithful reproductions of the signal in the optical power domain using narrowband illumination sources such as light emitting diodes (LEDs) or lasers diodes (LDs) centered at wavelengths $\lambda_1$ and $\lambda_2$. That is, the optical power of the emitter may vary linearly with the input signal. As shown in FIG. 10, a driver circuit 1002 converts the input signal to a current used to drive an LED 1004 such that, $P_{OPT} \approx K*I_{LED}$ where $P_{OPT}$ is the optical output power, $I_{LED}$ is the LED current, and K is a constant. LDs may be substituted for the LEDs.

The two light sources may be, but are not required to be, combined and collimated into a single beam 1006. Using a single beam addresses various aspects of calibrating the system and controlling stray light that could interfere with the detected signal. Measurements may be made without beam combining and/or collimation, but calibration and detection become more difficult. Beam combining and collimation may be implemented with, but is not limited to, a dichroic mirror, a randomized bifurcated fiber optic bundle, or a bi-color LED. A dichroic mirror (e.g., a 45 degree dichroic mirror) may combine two beams having different wavelengths. Dichroic mirrors have a transparent substrate (such as glass or sapphire) with an optical interference coating on one side and an optional anti-reflection coating on the other side. If precise overlap of the two beams is desired, two different wavelength LEDs may be remotely located and homogenized using a randomized bifurcated fiber optic bundle. The cable bundle has two inputs and one output. A bi-color LED may have two independently-controlled die in a common package.

The combined and collimated beams may be directed at the test object 1008. Light passing through the test object 1008 is absorbed and scattered. The radiation transmitted through the test object 1008 may be attenuated by many orders of magnitude. The radiation transmitted through the test object 1008 may optionally be collected by a condensing lens 1010 to increase the optical power on the detector assembly 300 and to provide spatial selectivity to the collected light. As shown in FIG. 10, a silicon PIN diode 1020 is used and is operative for wavelengths in the visible and near infrared (NIR) portions of the electromagnetic spectrum.

The photo-current generated by the PIN diode 1020 may be converted to a voltage signal. The voltage-to-current conversion may be accomplished by loading the PIN diode 1020 with a resistor. However, for high gain/low noise applications, a transimpedance amplifier 1030 may be provided. For improved signal-to-noise ratio (SNR), the gain of the transimpedance amplifier may be maximized within the bandwidth constraints of the system.

Additional gain may be supplied with a subsequent voltage amplifier 1040. This secondary stage may provide scaling of the signal, if desired, although a slight degradation in SNR occurs at the expense of this scaling stage.

Prior to down conversion, additional filtering 1050 may be needed to provide a DC block (analog), anti-aliasing (digital), and/or noise bandwidth restriction (analog/digital). In some instances, the secondary gain stage 1040 and filter stage 1050 may be combined.

The output of the filter stage is represented by:

$$V(t) = A \sin(2\pi f_0 t + \theta_{SIG}) + B \cos(2\pi f_0 t + \theta_{SIG}) \quad (E)$$

where
$\theta_{SIG}$=the phase of the signal at the output of the filter block,
A=the gain/attenuation of the I output of the quadrature reference propagating to this point,
B=the gain/attenuation of the Q output of the quadrature reference propagating to this point.

The outputs of the delay/phase rotation stages 1060 are:

$$\sin(2\pi f_0 t + \theta_{REF} + \theta) \quad (B)$$

$$\cos(2\pi f_0 t + \theta_{REF} + 0) \quad (G)$$

Multiplying 1070 the output of the filter stage (E) by the phase adjusted reference signals and removing the high frequency component with a low pass filter 1080 results in:

$$[A \sin(2\pi f t + \theta_{SIG}) + B \cos(2\pi f t + \theta_{SIG})]^* \sin(2\pi f_0 t + \theta_{REF} + \theta)$$
$$= \tfrac{1}{2} A \cos([f - f_0]t + \theta_{SIG} - \theta_{REF} - \theta) - \tfrac{1}{2} A \cos([f + f_0]t + \theta_{SIG} + \theta_{REF} + \theta) + \tfrac{1}{2} B \sin([f + f_0]t + \theta_{SIG} + \theta_{REF} + \theta) - \tfrac{1}{2} B \sin([f - f_0]t + \theta_{SIG} - \theta_{REF} - \theta) \quad (C)$$

$$\approx \tfrac{1}{2} A \cos([f - f_0]t + \theta_{SIG} - \theta_{REF} - 0) - \tfrac{1}{2} B \sin([f - f_0]t + \theta_{SIG} - \theta_{REF} - \theta) \quad (D)$$

Setting $\theta = \theta_{SIG} - \theta_{REF}$ $$\approx \tfrac{1}{2} A \cos([f - f_0]t) - \tfrac{1}{2} B \sin([f - f_0]t)$$

For $f = f_0$ (or near $f_0$)
$\approx \tfrac{1}{2}$ A at the I input to the analog-to-digital converter (ADC) 1090 and, $$[A \sin(2\pi f t + \theta_{SIG}) + B \cos(2\pi f t + \theta_{SIG})]\pi^* \cos(2\pi f_0 t + \theta_{REF} + \theta) = \tfrac{1}{2} A \sin([f - f_0]t + \theta_{SIG} - \theta_{REF} - \theta) + \tfrac{1}{2} A \cos([f + f_0]t + \theta_{SIG} + \theta_{REF} + \theta) + \tfrac{1}{2} B \cos([f - f_0]t + \theta_{SIG} - \theta_{REF} - \theta) - \tfrac{1}{2} B \cos([f + f_0]t + \theta_{SIG} + \theta_{REF} + \theta) \quad (C)$$

$$\approx \tfrac{1}{2} A \sin([f - f_0]t + \theta_{SIG} - \theta_{REF} - \theta) + \tfrac{1}{2} B \cos([f - f_0]t + \theta_{SIG} - \theta_{REF} - \theta) \quad (D)$$

setting $\theta = \theta_{SIG} - \theta_{REF}$ $$\approx \tfrac{1}{2} A \sin([f - f_0]t) + B \cos([f - f_0]t)$$

for $f = f_0$ (or near $f_0$)
$\approx \tfrac{1}{2}$ B at the Q input to the analog-to-digital converter (ADC) 1090.

In an alternative aspect, as shown in FIG. 11, the shaded blocks are implemented in the digital domain. These blocks may be implemented computationally (e.g. in software running on a digital signal processor (DSP)) or in logic (e.g. in a field programmable gate array (FPGA)). The filter block 1050 may implement the low pass, anti-aliasing filter prior to the ADC 1090. The output of the ADC 1090 represents a digitized version of the filter output (E). Multiplication 1100 may be handled computationally. The subsequent low-pass filter function may be implemented in software or digital hardware (e.g. FIR or IIR filter or directly using an FFT/DFT).

The phase delay 1060 may also be handled computationally or as a simple digital time delay. In use, it may not be necessary to apply both the I and Q reference signals to the detector. If a single reference is applied, it is possible re-generate the second.

The digital implementation of the down converter shown in FIG. 11 has several advantages over the analog implementation. First, the digital multiplication does not have the impairments (e.g. dc offset, clock leakage, and phase imbalance) common to analog multipliers. The impairments of the analog multiplier may require compensation means. Second, a digital phase delay may be balanced and immune to variations due to frequency and temperature. Third, the analog multiplier may be more expensive than DSPs and FPGAs.

It is noted that the down-conversion illustrated in FIGS. 10 and 11 to recover the I and Q components where the received signal (E) is multiplied by the reference signals (B) and (G) used to generate the transmitted signal is a realization of equations (1), (2), and/or (3) when integrated over the proper interval. The amplitude of the recovered signal is increased and the signal-to-noise ratio (SNR) is increased with longer integration times. In the digital domain the integration and subsequent LPF (low-pass filter) may be realized with an integrate and dump block as used in signal processing. In this regard, a Discrete Fourier Transform (DFT) is a synchronous down-converter when the sampling start is synchronized with the received signal (E). The coefficients for the DFT are to be taken from the normalized reference since a standard DFT would not recover the correct phase. Similarly, if using a Fast Fourier Transform (FFT), the coefficients may be optimized to use fixed twiddle factors that do not give the correct phase for the detected signal unless sampling is synchronized to start with the reference signal zero-crossing.

Regarding system phase calibration, to differentiate signals on I and Q, the phase of the reference signal may be corrected before the multiplier such that $\theta=\theta_{SIG}-\theta_{REF}=0$. Phase correction is a process in which disabling one source (e.g., enabling the $\lambda_1$ source while disabling the $\lambda_2$ source) reduces the system to a traditional lock-in amplifier. As such, the phase and amplitude of the $\lambda_1$ source to be measured as $\theta=\tan^{-1}(Q/I)$ and $R=(I^2+Q^2)^{1/2}$. In this case it is sufficient to adjust the phase until the Q component becomes sufficiently small. The calibration may be verified by disabling the $\lambda_1$ source and enabling the $\lambda_1$ source and verifying the I component is sufficiently small. Alternatively, phase of the reference signal (E) may be measured when there is no test object (e.g., an egg). The measured phase may be used as the reference. Absorption of $\lambda_1$ relative to $\lambda_2$ may be quantified relative to this initial reference phase.

Regarding amplitude calibration, the signal at the output of the filter block 1050 has been represented by:

$$V(t)=A\sin(2\pi ft+\theta_{SIG})+B\cos(2\pi ft+\theta_{SIG}) \qquad (E)$$

where:
A=the gain (attenuation) of the I output of the quadrature reference propagating to this point,
B=the gain (attenuation) of the Q output of the quadrature reference propagating to this point.

The A and B magnitude represent the product of the individual block gains which includes not only the test object 1008 but components of the instrumentation. While both the I and Q paths follow the same physical media once the light sources are combined at the beam combiner/collimation optic 1006, there is degree of variability to the output power and irradiance of the light emitter assembly 1004 as well as the coupling efficiency to the beam combiner/collimation optic 1006.

To compensate for the variability in the measurement system, a test object 1008 with a known response to the wavelengths may be measured and the performance of the test object 1008 subtracted from the measured response. A neutral density filter, with a known, wavelength invariant attenuation may be used. With such a filter, the coefficients A and B should be equal. Measurement results with the neutral density filter may be used to calculate correction factors for all subsequent measurements. For example, if A measured 0.4 and B measured 0.5, the B may be corrected relative to A on all subsequent measurements by multiply B by 0.5/0.4=1.25. During calibration, the neutral density filter may attenuate signal power to levels similar to those radiated from the intended test object for best results. Alternatively, calibration may be made directly by the detector provided sufficient dynamic range in the detector. Alternatively, a second (low gain) detector may be used to provide sufficient dynamic range.

In some applications, such as the use of multiple emitter-detector pairs for use in identifying the present condition of an avian egg at a high-throughput, the rejection on adjacent interfering signals in a multi-channel/multi-frequency detection system may be optimized with proper selection of the various reference frequencies. Integrating $$V_{SIG}*\sin(2\pi ft+\theta_{SIG})*\sin(2\pi f_0 t+\theta_{REF})\approx\tfrac{1}{2}V_{SIG}*\cos([f_0-f]t+\theta_{SIG}-\theta_{REF})$$

for $n/f_0$ seconds demonstrates perfect cancellation in an ideal system when $f=f_0/2n$, where n is the integration time expressed in the number of $f_0$ cycles. FIG. 12 provides an example where $f_0=10$ kHz and the signal is integrated for 500 μsec or n=5 cycles. In this case, the detector may provide a high level of rejection to signals on, or near, the 2 kHz null points.

Calibration may be made by making an offset calculation using a ND (neutral density) filter or by direct measurement. Measuring the response at $\lambda_1$ and $\lambda_2$ with the fixed attenuation of the neutral density filter allows the system performance to be normalized.

Transmitting on orthogonal vectors at the same frequency along the same signal path nulls out variations due to gain differences, group delay, temperature variation, as well as other variables introduced by using multiple frequencies or multiple signal paths. Advantageously, a single signal path avoids the cost associated with using multiple signal paths.

In some instances, a DC output error may be caused by the noise signal. This may appear as an offset or as a gain error. Since both effects are dependent upon the noise amplitude and frequency, they cannot be offset to zero in all cases and will limit the measurement accuracy. Because the errors are DC in nature, increasing the time constant does not help. Most commercially available lock-in amplifiers define tolerable noise as levels which do not affect the output more than a few percent of full scale.

The effects of quadrature error ($\Theta err$) are shown in FIG. 13. Considering signals A and B in near quadrature (i.e. nearly 90 degrees apart), and assuming the signal with amplitude A has the error and is misaligned with the I axis while the signal with amplitude B is perfectly aligned with Q, then the signal with amplitude A projects onto I a signal of $A*\cos(\Theta err)$ and projects onto Q a signal of $A*\sin(\Theta err)$. The lock-in amplifier is able to recover the projection onto I of $A*\cos(\Theta err)$. However, the projection onto Q of $A*\sin(\Theta err)$ is an interring signal that cannot be distinguished from B by the lock-in amplifier. This projection also cannot be distinguished by any other means (e.g. FFT). The interference due to quadrature error may be low-enough so as not to limit the measurement.

The signal-to-interference ratio (S/I) resulting from quadrature error may be calculated as:

$$S/I=B/(A*\sin(\Theta err))$$

Table 1 below calculates the measurement floor as limited by quadrature error for different amplitudes of B and A. It is noted that even with large amplitude difference (A/B=10), signal rejection in excess of 35 dB may be achieved.

TABLE 1

| B | A | $\Theta err$ (deg) | sin ($\Theta err$) | S/I = B/A*sin ($\Theta err$) | S/I (dB) |
|---|---|---|---|---|---|
| 1 | 1 | 1 | 0.017452 | 57.30 | 35.16 |
| 1 | 1 | 0.1 | 0.001745 | 572.96 | 55.16 |
| 1 | 10 | 1 | 0.017452 | 5.73 | 15.16 |
| 1 | 10 | 0.1 | 0.001745 | 57.30 | 35.16 |

FIG. 14 shows the optical density (OD) of different egg types versus wavelength (in nanometers) of transmitted light. Optical density is a logarithmic scale with each additional integer value representing an order of magnitude reduction in the transmitted light. Comparing the variation in optical density between 800 nm and 925 nm (the wavelengths of interest), variations in signal amplitudes at the two wavelengths may be expected to vary about an order of magnitude maximum. Referring now to the two points (810, 910) shown in FIG. 14, it is shown that the slope of the line between them reverses for rotten eggs and live eggs. A ratio calculation from these two points is therefore sufficient to differentiate between a rotten egg and a live egg.

FIGS. 17 and 18 illustrate the measured relationship between filter bandwidth and signal noise for the SR850 lock-in amplifier, where the time constant (TC) setting is plotted versus the signal. The TC settings are as follows: 2=100 μs; 3=300 μs; 4=1 ms; 5=3 ms; 6=10 ms; 7=30 ms; and 8=100 ms. The filter settings are as follows: 0=6 dB/oct; 1=12 dB/oct; 2=18 dB/oct; 3=24 dB/oct.

Figure 20:
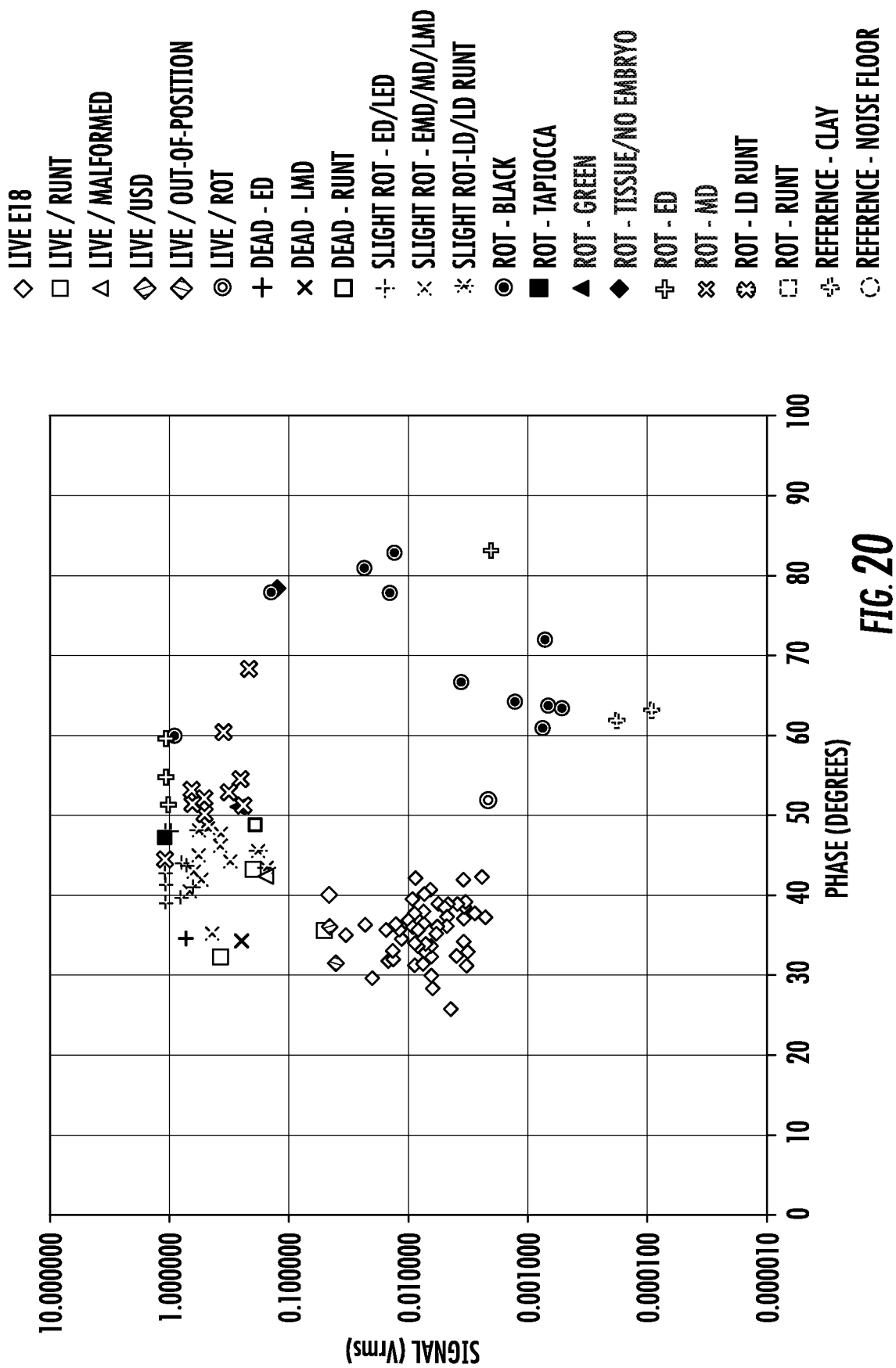
Figure 21:
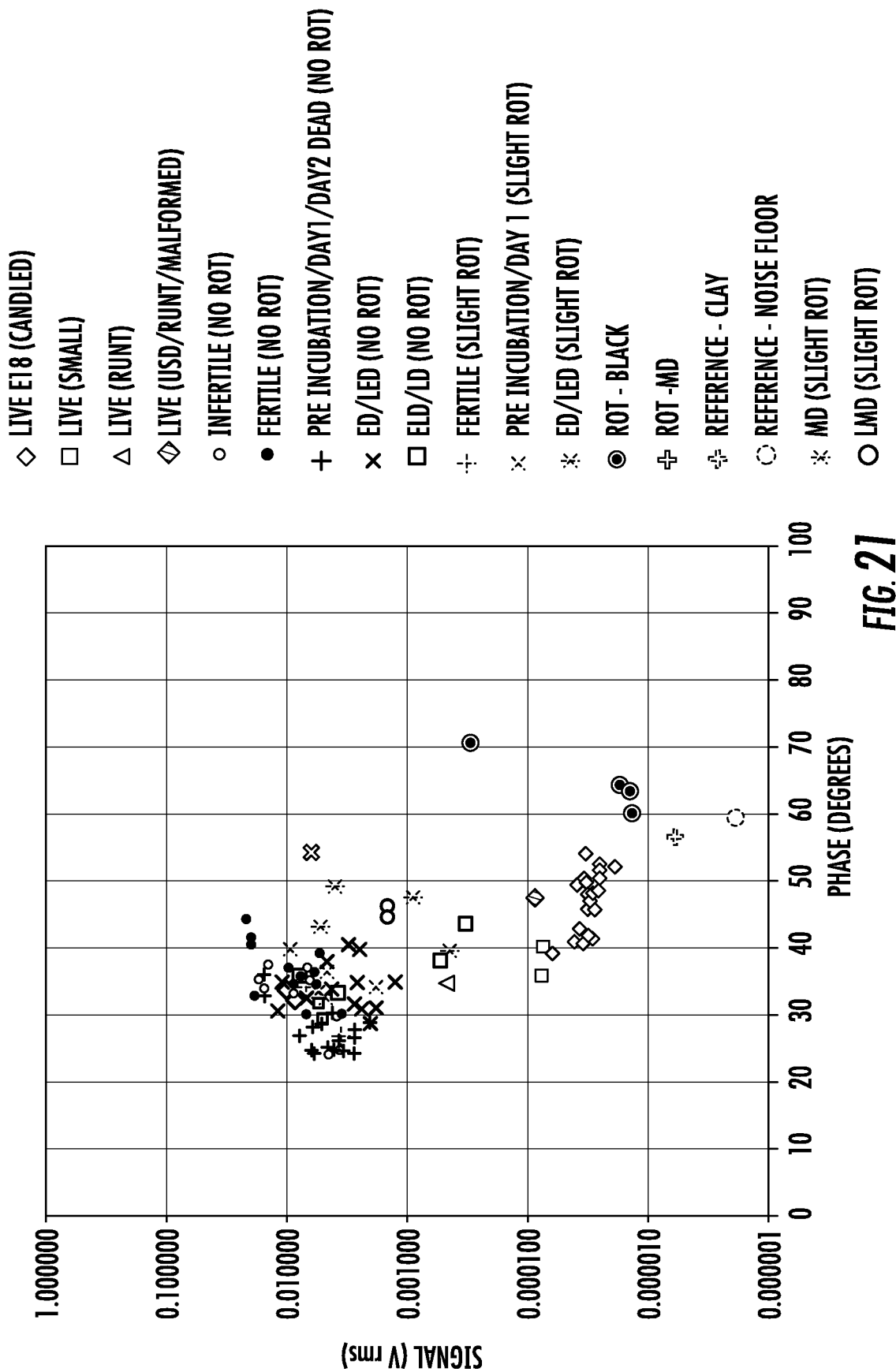
Figure 22:
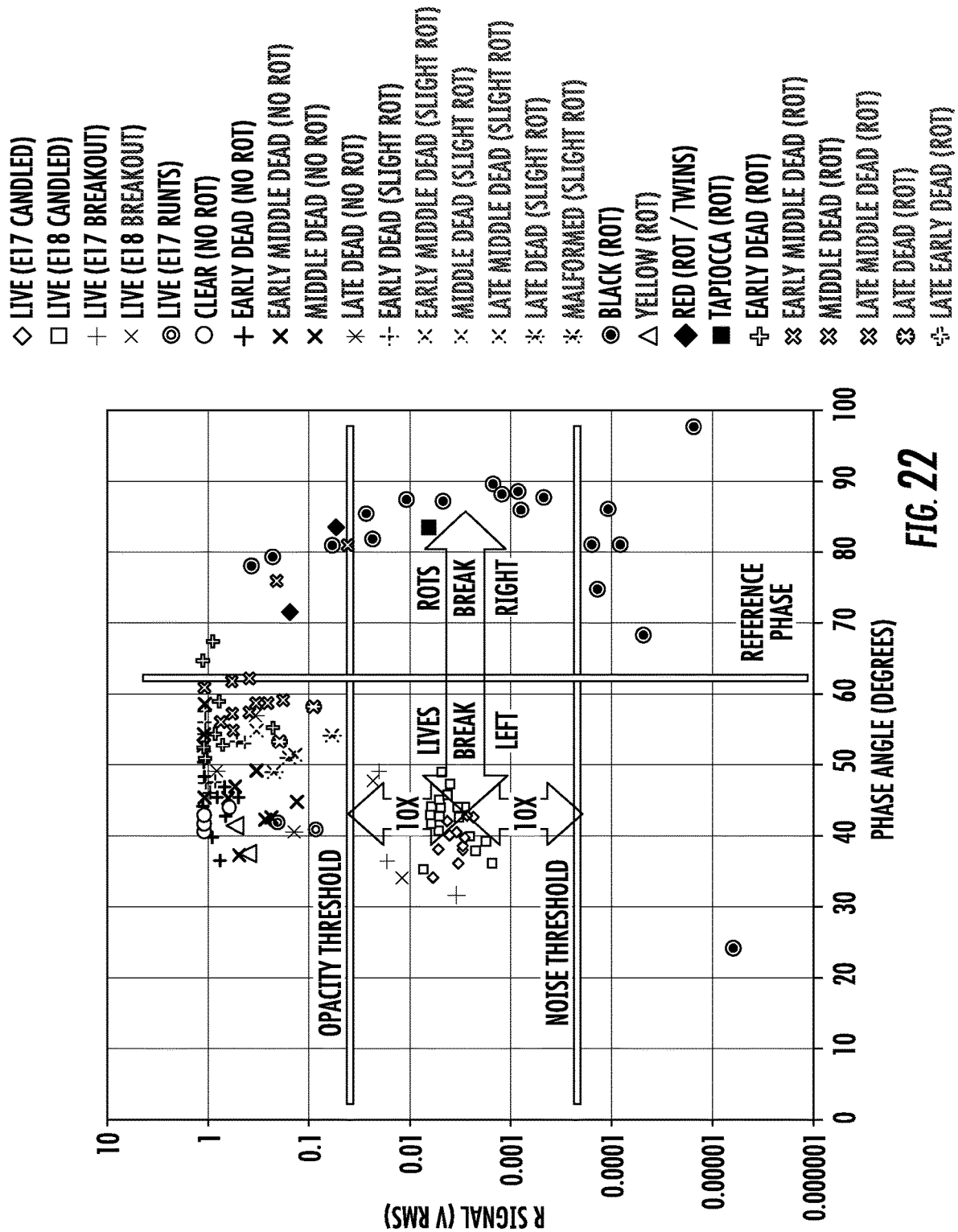

Once the magnitude (R) and phase (θ) are recovered from the received signal (E) for each egg, the magnitude (R) and phase (θ) may be transferred into polar coordinates and plotted against each other, as shown in FIGS. 15, 16 and 19-22. As shown, the live eggs separate from the non-live eggs when plotted. As such, threshold levels may be set, as shown in FIG. 22, such that eggs are identified or determined as viable or non-viable based on such threshold levels with respect to magnitude (R) and phase (θ) of the received signal. Threshold values may be determined by a calibration process such that there is maximum separation between lives and non-lives during the detection process. Actual threshold values may be dependent on the actual electronics and optics employed in the system that is implemented. Having the first and second sources at about the same power provides improved discrimination.

EXAMPLES

A laboratory prototype was constructed and used in several trials. A schematic is shown in FIG. 5.

Quadrature Reference Clocks $$\sin(2\pi f_0 + \theta_{REF}) \text{ and} \quad (A)$$

$$\cos(2\pi f_0 + \theta_{REF}) \quad (F)$$

were generated using a Tektronix AFG 3022C Arbitrary Function Generator 70. These two references have arbitrary absolute phase $\theta_{REF}$ but have a relative phase of 90° to each other. The reference signal (A) and (F) are used as modulating signals to a pair of Stanford Research Systems LDC 501 Laser Diode Controllers 75, 80 creating faithful reproductions of each signal in the optical power domain with low total harmonic distortion (THD). That is, the optical power output of the illumination source varies linearly with the input signal; $P_{OPT} \approx K^* I_{DRIVE}$ where $P_{OPT}$ is the optical output power, $I_{DRIVE}$ is the drive current through the illumination source, and K is a constant.

In testing, the laser diode controllers 75, 80 were used to drive the following narrowband illumination sources at the indicated wavelengths:

Light Emitting Diode (LED) Combinations
  OSRAM SFH 4780S 680 mW, 810 nm
  Marubeni SMBB910D-1100, 470 mW, 910 nm
Lasers Diode (LD) Combinations
  ThorLabs L808P010 10 mW, 808 nm
  ThorLabs M5-905-0100 100 mW, 905 nm
  Collimation lenses 205 and 207 were used when using both LEDs and LDs to minimize the beam dispersion and unwanted stray light. A Semrock LPD02-830RU-25 45 degree dichroic mirror 209 with a sharp cutoff wavelength of 830 nm was used to combine the two illumination sources into a single beam. The combined and collimated beams were directed at the test objects (E17-E19 chicken eggs 1 of different known states (Live, Rotted, and Dead)).

The radiation transmitted through the test object was collected by a series of three condensing lens to increase the optical power transfer between the test object and the detector and to minimize light outside the +/−12 degree acceptance cone.

The detector 300 used in testing was a Vishay TEM5110X01 Silicon PIN Diode. The photo-current generated by the PIN diode was converted to a voltage signal using a Texas Instruments OPA380 high speed, transimpedance amplifier.

The output of the second gain stage (9) is represented by:

$$V(t) = A\sin(2\pi f_0 + \theta_{SIG}) + B\cos(2\pi f_0 + \theta_{SIG}) \quad (E)$$

where
  $\theta_{SIG}$=the phase of the signal at the output of the filter block,
  A=the gain/attenuation of the I output of the quadrature reference propagating to this point,
  B=the gain/attenuation of the Q output of the quadrature reference propagating to this point.

Magnitude (R) and phase (θ) were recovered from the received signal (E) using a SR850 Lock-In amplifier 95.

Phase calibration was maintained by connecting the synchronization output signal from the TEK AFG 3022C to the SRS SR850 External Reference Input (B). By turning off the Q source (905 nm LD/910 nm LED), the SR850 phase aligned with the I source (808 nm LD/810 nm LED) using a calibration feature of the instrument.

FIG. 15 plots phase angle (θ) against signal power (magnitude (R)) for 120 eggs subjected to the disclosed method at Day 18 of incubation. Each egg was positioned on a light sealing stand. Laser diodes (808 nm and 904 nm) were used as the light emitter sources. The time constant (TC) was set at 100 ms.

FIG. 16 plots phase angle (θ) against signal power (magnitude (R)) for 216 eggs subjected to the disclosed method at Day 17 and Day 18 of incubation. Each egg was positioned on a light sealing stand. Laser diodes (808 nm and 904 nm) were used as the light emitter sources. The time constant (TC) was set at 100 ms.

Figure 19:
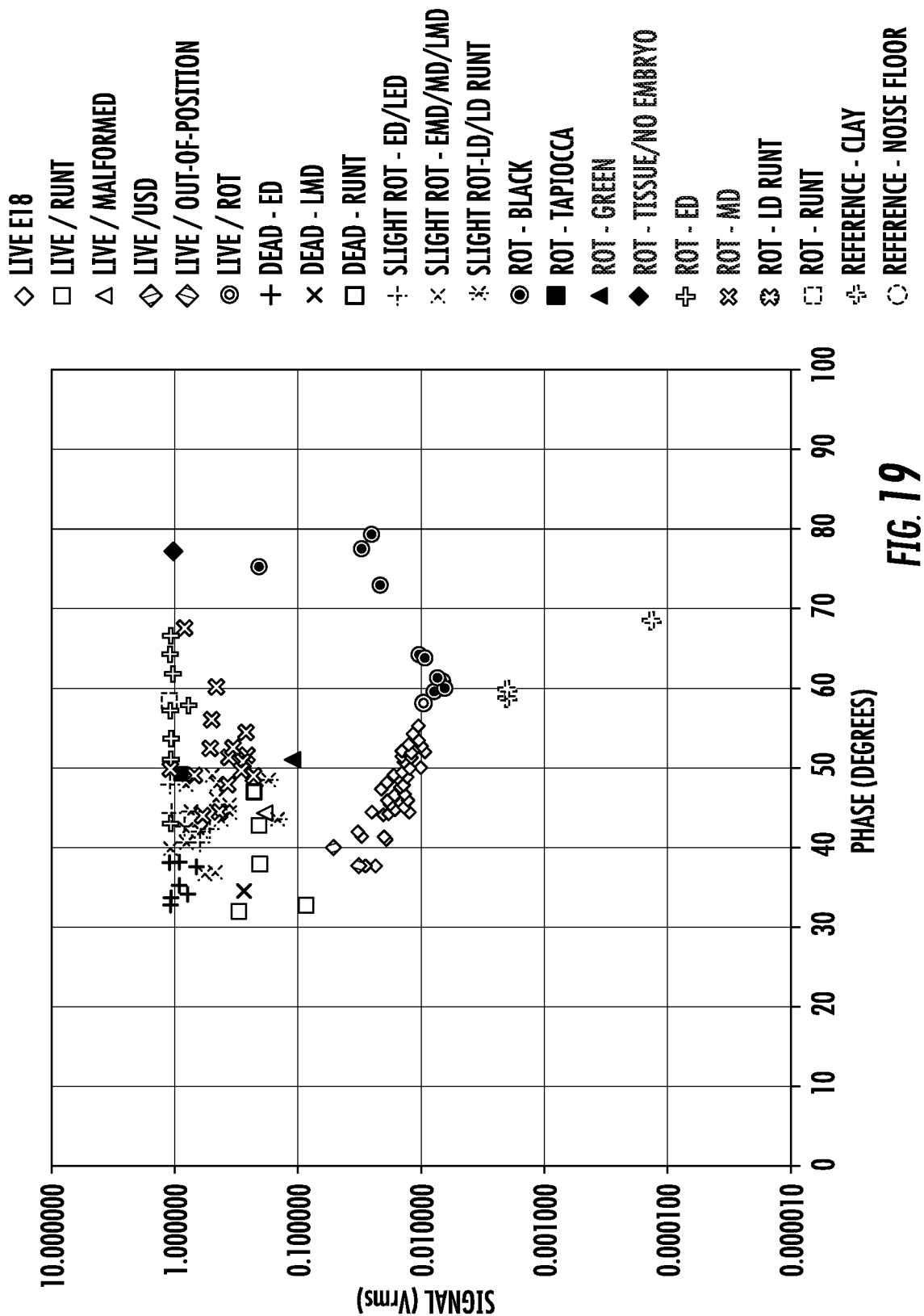

FIG. 19 plots phase angle (θ) against signal power (magnitude (R)) for 168 eggs subjected to the disclosed method at Day 17 and Day 18 of incubation. The eggs were positioned in an egg flat when subjected to the analysis. Laser diodes (808 nm and 904 nm) were used as the light emitter sources. The time constant (TC) was set at 100 ms, with a filter setting of "1". No attempt was made to control self-interfering light.

FIG. 20 plots phase angle (θ) against signal power (magnitude (R)) for 168 eggs subjected to the disclosed method at Day 17 and Day 18 of incubation. The eggs were positioned in an egg flat when subjected to the analysis. A half inch tall section of ¾ inch PVC pipe was extended up to but not touching the egg flat. Laser diodes (808 nm and 904 nm) were used as the light emitter sources. The time constant (TC) was set at 100 ms, with a filter setting of "1".

FIG. 21 plots phase angle (θ) against signal power (magnitude (R)) for 168 eggs subjected to the disclosed method at Day 17 and Day 18 of incubation. The eggs were positioned in an egg flat when subjected to the analysis.

Laser diodes (808 nm and 904 nm) were used as the light emitter sources. The time constant (TC) set at 100 ms, with a filter setting of "1".

FIG. 22 plots phase angle (θ) against signal power (magnitude (R)) for 168 eggs subjected to the disclosed method at Day 17 and Day 18 of incubation. The eggs were positioned in an egg flat when subjected to the analysis. Laser diodes (808 nm and 904 nm) were used as the light emitter sources. The time constant (TC) was set at 100 ms, with a filter setting of "8".

Many modifications and other aspects of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. An apparatus for non-invasively identifying a present condition of an egg, the apparatus comprising:
    an emitter assembly configured to emit light toward an egg, the emitter assembly having a first emitter source configured to emit a first light signal and a second emitter source configured to emit a second light signal, the first and second light signals being emitted simultaneously and combined into a combined light signal and being transmitted through the egg in phase quadrature;
    a detector assembly configured to detect the combined light signal transmitted through the egg, and further being configured to increase optical power, the detector assembly having a transimpedance amplifier configured to amplify the combined light signal and improve signal-to-noise ratio to the combined light signal in order to simultaneously filter and resolve a relative amplitude or an absolute amplitude of each of the first and second light signals in the detector assembly; and
    a processor programmed to process the detected first and second light signals to identify a present condition of the egg using at least one of the relative amplitudes or absolute amplitudes of the first and second light signals.

2. An apparatus according to claim 1, wherein the first light signal is emitted at a first wavelength and the second light signal is emitted at a second wavelength different than the first wavelength.

3. An apparatus according to claim 2, wherein the first emitter source is configured to emit light in the range of about 780-830 nanometers, and the second emitter source is configured to emit light in the range of about 850-940 nanometers.

4. An apparatus according to claim 1, wherein the first and second light signals are transmitted at a common frequency.

5. An apparatus according to claim 1, wherein the detector assembly includes a phase-sensitive detector.

6. An apparatus according to claim 1, wherein the detected first and second light signals are processed and plotted on a polar coordinate system and assessed against threshold levels to determine the present condition of the egg.

7. An apparatus according to claim 1, wherein the detected first and second light signals are processed as a function of signal amplitude indicative of a living embryo within the egg.

8. An apparatus according to claim 1, further comprising a plurality of emitter assemblies and detector assemblies, forming a plurality of emitter-detector pairs, wherein the emitters transmit signals with orthogonal frequency relationships.

9. A method of analyzing a present condition of an egg, the method comprising:
    simultaneously transmitting a first light signal and a second light signal, the first and second light signals being combined into a combined light signal and in phase quadrature through the egg to be analyzed;
    detecting the combined light signal transmitted through the egg;
    increasing optical power in a detector assembly;
    amplifying the combined light signal with a transimpedance amplifier of the detector assembly, thereby improving signal-to-noise ratio to the combined light signal for simultaneously filtering and resolving a relative amplitude or an absolute amplitude of each of the first and second light signals in the detector assembly; and
    determining a present condition of the egg using at least one of the relative and absolute amplitudes of the first and second light signals.

10. A method according to claim 9, wherein transmitting a first light signal and a second light signal further comprises transmitting a first light signal and a second light signal at different wavelengths.

11. A method according to claim 10, wherein the first light signal is transmitted in the range of about 780-830 nanometers, and the second light signal is transmitted in the range of about 850-940 nanometers.

12. A method according to claim 9, wherein transmitting a first light signal and a second light signal further comprises transmitting a first light signal and a second light signal at a common frequency.

13. A method according to claim 9, wherein determining a present condition of the egg further comprises processing and plotting extracted amplitude and phase data on a polar coordinate system and assessing against threshold levels to determine the present condition of the egg.

14. A method according to claim 9, wherein determining a present condition of the egg further comprises determining the amplitude modulation of the detected first and second light signals as being indicative of the egg containing a live embryo.

* * * * *